United States Patent [19]
Slightom et al.

[11] Patent Number: 5,998,699
[45] Date of Patent: *Dec. 7, 1999

[54] POTYVIRUS COAT PROTEIN GENES AND PLANTS TRANSFORMED THEREWITH

[75] Inventors: Jerry L. Slightom; Hector D. Quemada, both of Kalamazoo, Mich.; Dennis Gonsalves, Geneva, N.Y.; Brigitte L'hostis, Paris, France

[73] Assignees: Seminis Vegetable Seeds, Inc., Saticoy, Calif.; Cornell Research Foundation, Inc., Ithaca, N.Y.

[ * ] Notice: This patent is subject to a terminal disclaimer.

[21] Appl. No.: 08/358,653

[22] Filed: Dec. 19, 1994

Related U.S. Application Data

[63] Continuation of application No. 08/232,846, Apr. 25, 1994, abandoned, which is a continuation of application No. 08/013,971, Feb. 4, 1993, abandoned, which is a continuation of application No. 07/656,167, Feb. 19, 1991, abandoned, which is a continuation of application No. PCT/US89/03094, Jul. 20, 1989, which is a continuation of application No. 07/368,710, Jun. 19, 1989, abandoned, which is a continuation-in-part of application No. 07/234,412, Aug. 19, 1988, abandoned, and a continuation of application No. 07/323,536, Mar. 14, 1989, abandoned.

[51] Int. Cl.⁶ .............................. A01H 5/00; A01H 5/10; C12N 5/14; C12N 15/40; C12N 15/82
[52] U.S. Cl. .................. 800/205; 435/172.3; 435/419; 536/23.72; 800/205; 800/250; 800/255; 800/DIG. 9; 800/DIG. 18; 800/DIG. 23; 800/DIG. 40
[58] Field of Search ............... 536/23.72; 435/240.4, 435/172.3, 320.1, 252.3, 419; 800/205, 250, 255, DIG. 9, DIG. 18, DIG. 23, DIG. 40

[56] References Cited

FOREIGN PATENT DOCUMENTS

| | | |
|---|---|---|
| 0 223 452 | 5/1987 | European Pat. Off. . |
| 0223452 | 5/1987 | European Pat. Off. ............... 800/205 |
| PCT/US86/ 00514 | 7/1986 | WIPO . |
| 8707644 | 12/1987 | WIPO ..................................... 536/27 |

OTHER PUBLICATIONS

Yu, et al. (1989) Biological Abstracts 88: Abstract No. 44985 (and Arch Virol. 105 : 55–64 See p. 3).
Grumet, et al. (Jun. 1988) Hortscience 23 (3): 755, abstract No. 260.
L'Hostis, et al. (1987) Phytopathology 77(1): 119.
Yeh, et al. (1985) Virology 143 :260–271.
Nagel, et al (1985) Virology 143 : 435–441.
Qutcke, et al (Jan. 1987) The EMBO Journal 6: 43–48.
Barton, et al. (1987) Plant Physiology 85 : 1103–1109.
Gallie, et al. (1987) Nucleic Acids Research 15 (8): 3257–3273.
Shintaku (1991) Journal of Gen. Virology 72 : 2587–2589.
Yu et al (1989) Arch Virol. 105 : 55–64.
Wilson, et al (Apr. 15, 1993) Proc. Natl. Acad. Sci, USA 90 (8): 3134–3141.
Cuozzo et al., Biotechnology, 1988, vol. 6, pp. 549–557.
Quemada, et al. J. Gen. Virol., 1990, 71 : 1451–1460.
Greber, Aust. J. Agric. Res. vol. 29, pp. 1235–1245 (1978).
Purcifull, et al., CMI/AAB Description of Plant Viruses, 1984, No. 292.
Allison et al. (1985) "Biochemical Analysis of the Capsid Protein Gene and Capsid Protein of Tobacco Etch Virus: N–Terminal Amino Acids Are Located on the Virion's Surface", Virology 147:309–316 (1985).
Allison et al. (1986) "The Nucleotide Sequence of the Coding Region of Tobacco Etch Virus Genomic RNA: Evidence for the Synthesis of a Single Polyprotein", Virology 154:9–20 (1986).
Carrington, J.C. and Dougherty, W.G. (1987) "Small nuclear inclusion protein encoded by a plant potyvirus genome is a protease", J. Virology 61:2540–2548 (1987).
Dodds et al. (1985) "Cross Protection between strains of cucumber mosaic virus: effect of host and type of inoculum on accumulation of virions and double–stranded RNA of the challenge strain", Virology 144:301–309 (1985).
Dougherty, W.G. et al. (1985) "Nucleotide Sequence at the 3' Terminus of Pepper Mottle Virus Genomic RNA: Evidence for an Alternative Mode of Potyvirus Capsid Protein Gene Organization", Virology 146:282–291 (1985).
Dougherty, W.G. et al. (1988) "Biochemical and mutatinal analysis of plant virus polyprotein cleavage site", EMBO J. 7:1281–1287 (1988).
Dougherty, W. G. and Carrington, J. C. (1988)"Expression and function of potyviral gene products", Ann. Rev. Phytopathol. 26:123–143 (1988).
Eggenberger, A. L. et al. (1989) "The nucleotide sequence of a Soybean Mosaic Virus Coat Protein region and its expression in *Escherichia coli, Agrobacterium tumefaciens, and tobacco callus*", Virology, in press (1989).
Hinchee, M. A. W. et al (1988) "Production of transgenic soybean plants using Agrobacterium–mediated DNA transfer", Bio/tech. 6:915–921 (1988).
Kozak, M. (1986) "Point mutations define a sequence flanking the Aug initiator codon that modulates translation by eukaryotic ribsomes", Cell 44:283–292 (1986).
Loesch–Fries et al. (1987) "Expression of alfalfa mosaic virus RNA 4 in transgenic plants confers virus resistance", EMBO J 6:1845–1851 (1987).

(List continued on next page.)

*Primary Examiner*—Douglas W. Robinson
*Assistant Examiner*—Amy J. Nelson
*Attorney, Agent, or Firm*—Rockey, Milnamow & Katz, Ltd.

[57] ABSTRACT

The present invention relates to the coat protein genes of Papaya Ringspot Virus Strain papaya ringspot (PRV-p), Watermelon Mosaic Virus II (WMVII), and Zucchini Yellow Mosaic Virus (ZYMV); to expression vectors which contain a coat protein gene for PVP-p, WMVII or ZYMV, and, additionally, the necessary genetic regulatory sequences needed for expression of a gene transferred into a plant; to bacterial or plant cells which are transformed with an expression vector containing the PVP-p, WMVII or ZYMV coat protein genes; to transgenic plants which are produced from plant cells transformed with an expression vector containing the coat protein gene from PVP-p, WMVII or ZYMV; and to a process of producing transgenic plants which have increased resistance to viral infection.

14 Claims, 18 Drawing Sheets

OTHER PUBLICATIONS

Pietrzak et al. (1986) "Expression in plants of two bacterial antibiotic resistant genes after protoplast transformation with a new plant expression vector", Nucleic Acids Research 14:5857–5868 (1986).

Powell–Abel et al. (1986) "Delay of disease development in transgenic plants that express the tobacco mosaic virus coat protein gene", Science 232:738–743 (1986).

Quemada, H. D. et al. (1989) "The nucleotide sequences of cDNA clones from RNA3 of Cucumber Mosaic Virus strains C and WL", J. Gen. Virol. 70:1065–1073 (1989).

Shukla, D. D. et al. (1986) "Coat Proteins of Potyviruses", Virology 152:118–125 (1986).

Shukla, D. D. et al. (1988) "The N and C termini of the Coat Proteins of Potyviruses Are Surface–located and the N Terminus Contains the Major Virus–specific Epitopes", J. Gen. Virol. 69:1497–1508 (1988).

Turner et al. (1987) "Expression of alfalfa mosaic virus coat protein gene confers cross–protection in transgenic tobacco and tomato plants", EMBO J. 6:1181–1188 (1987).

Yeh and Gonsalves (1985) "Translation of Papaya Ringspot Virus RNA in vitro: Detection of a Possible Polyprotein That is Processed for Capsid Protein, Cylindrical–Inclusion Protein, and Amorphous–Inclusion Protein", Virology 143:260–271 (1985).

An et al. (1985) "New cloning vehicles for transformation of higher plants", EMBO J. 4:277–285 (1985).

An, G. (1986) "Development of plant promoter expression vectors and their use for analysis of differential activity of nopaline synthase promoter in transformed tobacco cells", Plant Physiol. 81:86–91 (1986).

Bevan et al. (1983) "Structure and transcription of the nopaline synthase gene region of T–DNA", Nucleic Acids Research 11:369–385 (1983).

Depicker et al. (1982) "Nopaline synthase: transcript mapping and DNA sequence", J. Mol. Appl. Genet. 1:561–573 (1982).

Hepburn, A. et al. (1985) "The use of pNJ5000 as an intermediate vector for genetic manipulation of Agrobacterium Ti–plasmids", J. General Microbio. 131:2961–2969 (1985).

Klein et al., (1987) "High–velocity microprojectiles for delivering nucleic acids into living cells", Nature 327:70–73 (May 1987).

Klein et al., (1988) "Factors influencing gene delivery into Zea mays cells by high–velocity microprojectiles", Bio/tech. 6:559–563 (May 1988).

Mazur, B. J. and Chui, C.–F. (1985) "Sequence of a genomic DNA clone for the small subunit of ribulose bis–phosphate carboxylase–oxygenase from tobacco", Nucleic Acids Research 13:2373–2386 (1985).

McCabe, D. E., et al., (1988) "Stable transformation of soybean (Glycine max) by particle acceleration", Bio/tech. 6:923–926 (1988).

Olsen, M. K. et al (1989) "Enhancement of heterologous polypeptide expression by alterations in the ribosome–binding–site sequence", J. Biotech. 9:179–190 (1989).

Slightom et al. (1983) "Complete nucleotide sequence of a French bean storage protein gene: Phaseolin", Proc. Natl. Acad. Sci. U.S.A. 80:1897–1901 (Apr. 1983; and.

Vilaine, F. and Casse–Delbart, F. (1987) "Independent induction of transformed roots by the TL and TR regions of the Ri plasmid of agropine type Agrobacterium rhizogenes", Mol. Gen. Genet. 206:17–23 (1987).

Phytopatology, vol. 77, No. 1, 1987, B. L'Hostis et al. "Synthesis and cloning of a DNA complementary to a mild mutant of papaya ringspot virus," p. 119.

Hortscience, vol. 23, No. 3, Jun. 1988, R. Grumet et al. "Purification and cloning of zucchini yellow mosaic virus," p. 755, abstract No. 260.

Biological Abstracts, vol. 88, 1989, M.H. Yu et al. "Cost protein of potviruses: 6. Amino acid sequences suggest watermelon mosaic virus 2 and soybean mosaic virus N are strains of the same potyvirus," abstract No. 44985, & Arch. Virol. 105(1/2): 55–64, 1989.

Journal of Cellular Biochemistry, UCLA Symposia on Molecular & Cellular Biology, Abstracts of the 17th Annual Meetings, Feb. 28—Apr. 10, 1988, Supplement 12c, 1988, Alan R. Liss, Inc. (New York, US), A.L. Eggenberger et al.: "cDNA cloning, sequencing, and expression of the soybean mosaic virus coat protein coding sequence," p. 274, abstract No. Y 240.

FIGURE 1A

```
        ↓
        CAGTCCAAGAATGAAGCTGTGGATGCTGGTTTGAATGAAAAACTCAAAGAGAAGGAAAAT
  1     ---------+---------+---------+---------+---------+---------+    60
        GlnSerLysAsnGluAlaValAspAlaGlyLeuAsnGluLysLeuLysGluLysGluAsn

CAGAAAGAAAAAGAAAAAGAAAAACAAAAGAGAAAGAAAAAGACGGTGCTAGTGACGGA
 61     ---------+---------+---------+---------+---------+---------+   120
        GlnLysGluLysGluLysGluLysGlnLysGluLysGluLysAspGlyAlaSerAspGly

AATGATGTGTCAACTAGCACAAAAACTGGAGAGAGAGATAGAGATGTCAATGTTGGGACC
121     ---------+---------+---------+---------+---------+---------+   180
        AsnAspValSerThrSerThrLysThrGlyGluArgAspArgAspValAsnValGlyThr

AGTGGAACTTTCACTGTTCCGAGAATTAAATCATTTACTGATAAGATGGTTCTACCGAGA
181     ---------+---------+---------+---------+---------+---------+   240
        SerGlyThrPheThrValProArgIleLysSerPheThrAspLysMetValLeuProArg

ATTAAGGGGAAGACTGTCCTTAATTTAAATCATCTTCTTCAGTACAATCCGCAACAAATT
241     ---------+---------+---------+---------+---------+---------+   300
        IleLysGlyLysThrValLeuAsnLeuAsnHisLeuLeuGlnTyrAsnProGlnGlnIle

GACATTTCTAACACTCGTGCCACTCATTCACAATTTGAGAAGTGGTATGAGGGAGTGAGG
301     ---------+---------+---------+---------+---------+---------+   360
        AspIleSerAsnThrArgAlaThrHisSerGlnPheGluLysTrpTyrGluGlyValArg

AATGATTATGGCCTTAATGATAATGAAATGCAAGTGATGCTAAATGGTTTGATGGTTTGG
361     ---------+---------+---------+---------+---------+---------+   420
        AsnAspTyrGlyleuAsnAspAsnGluMetGlnValMetLeuAsnGlyLeuMetValTrp TGTATCGAGAATGGTACATCTCCAGACATATCTGGTGTCTGGGTTATGATGGATGGGGAA
421     ---------+---------+---------+---------+---------+---------+   480
        CysIleGluAsnGlyThrSerProAspIleSerGlyValTrpValMetMetAspGlyGlu ACCCAAGTTGATTATCCAATCAAGCCTTTGATTGAGCATGCTACTCCGTCATTTAGGCAA
481     ---------+---------+---------+---------+---------+---------+   540
        ThrGlnValAspTyrProIleLysProLeuIleGluHisAlaThrProSerPheArgGln ATTATGGCTCACTTTAGTAACGCGGCAGAAGCATACATTGCGAAGAGAAATGCTACTGAG
541     ---------+---------+---------+---------+---------+---------+   600
        IleMetAlaHisPheSerAsnAlaAlaGluAlaTyrIleAlaLysArgAsnAlaThrGlu
```

FIGURE 1B

```
       AGGTACATGCCGCGGTATGGAATCAAGAGAAATTTGACTGACATTAGCCTCGCTAGATAC
601    ---------+---------+---------+---------+---------+---------+ 660
       ArgTyrMetProArgTyrGlyIleLysArgAsnLeuThrAspIleSerLeuAlaArgTyr

GCTTTCGACTTCTATGAGGTGAATTCGAAAACACCTGATAGGGCTCGCGAAGCTCACATG
661    ---------+---------+---------+---------+---------+---------+ 720
       AlaPheAspPheTyrGluValAsnSerLysThrProAspArgAlaArgGluAlaHisMet

CAGATGAAGGCTGCAGCGCTGCGAAACACCAGTCGCAAAATGTTTGGTATGGACGGCAGT
721    ---------+---------+---------+---------+---------+---------+ 780
       GlnMetLysAlaAlaAlaLeuArgAsnThrSerArgLysMetPheGlyMetAspGlySer

GTTAGTAACAAGGAAGAAAACACGGAGAGACACACAGTGGAAGATGTCAATAGAGACATG
781    ---------+---------+---------+---------+---------+---------+ 840
       ValSerAsnLysGluGluAsnThrGluArgHisThrValGluAspValAsnArgAspMet

CACTCTCTCCTGGGTATGCGCAACTAAATACCTGCGCTTGTGTGTTTGTTGAGTCTGACT
841    ---------+---------+---------+---------+---------+---------+ 900
       HisSerLeuLeuGlyMetArgAsnEnd

CGACCCTGTTTCACCTTATGGTACTATATAAGCATTAGAATACAGAGTGGCTGCGCCACC
901    ---------+---------+---------+---------+---------+---------+ 960

GCTTCTATTTTACAGTGAGGGTAGCCCTCCGTGCTTTTAGTATTATTCGAGTTCTCTGAG
961    ---------+---------+---------+---------+---------+---------+ 1020

TCTCCATACAGTGTGGGTGGCCCACGTGATATTCGAGCCTCTTAGAATGAGAAAAAAAAA
1021   ---------+---------+---------+---------+---------+---------+ 1080

AAAAAAAAAAAAAAAAAAAAAAAAAAAAAAAAAAAAAGGAATTCC
1081   ---------+---------+---------+---------+----    1124
```

FIGURE 2A

```
      GTGTCTTTACAATCAGGAAAAGAAACAGTTGAAAATTTGGACGCAGGGAAAGAATCAAAG
  1   ---------+---------+---------+---------+---------+---------+  60
      ValSerLeuGlnSerGlyLysGluthrValGluAsnLeuAspAlaGlyLysGluSerLys AAAGATGCCAGTGACAAAGGGAATAAGCCGCAGAACTCGCAAGTTGGTCAGGGTAGCAAG
 61   ---------+---------+---------+---------+---------+---------+ 120
      LysAspAlaSerAspLysGlyAsnLysProGlnAsnSerGlnValGlyGlnGlySerLys GAACCAACAAAAACCGGCACAGTCAGCAAGGATGTAAATGTTGGATCGAAAGGAAAAGAA
121   ---------+---------+---------+---------+---------+---------+ 180
      GluProThrLysThrGlyThrValSerLysAspValAsnValGlySerLysGlyLysGlu GTCCCACGACTACAAAAGATAACAAAGAAAATGAATCTTCCAACAGTTGGTGGGAAAATC
181   ---------+---------+---------+---------+---------+---------+ 240
      ValProArgLeuGlnLysIleThrLysLysMetAsnLeuProThrValGlyGlyLysIle ATTCTTAGCTTAGACCATTTGCTTGAGTACAAACCTAGTCAAGTTGATTTGTTTAACACT
241   ---------+---------+---------+---------+---------+---------+ 300
      IleLeuSerLeuAspHisLeuLeuGluTyrLysProSerGlnValAspLeuPheAsnThr CGAGCAACAAAAACACAATTTGAATCATGGTACAGCGCAGTCAAAGTTGAGTATGATCTT
301   ---------+---------+---------+---------+---------+---------+ 360
      ArgAlaThrLysThrGlnPheGluSerTrpTyrSerAlaValLysValGluTyrAspLeu AATGATGAGCAAATGGGTGTGATTATGAATGGTTTTATGGTTTGGTGTATCGATAACGGT
361   ---------+---------+---------+---------+---------+---------+ 420
      AsnAspGluGlnMetGlyValIleMetAsnGlyPheMetValTrpCysIleAspAsnGly ACATCTCCAGATGTCAATGGAGTGTGGGTAATGATGGATGGGGAAGAGCAAGTTGAGTAC
421   ---------+---------+---------+---------+---------+---------+ 480
      ThrSerProAspValAsnGlyValTrpValMetMetAspGlyGluGluGlnValGluTyr CCACTAAAGCCAATTGTTGAAAATGCAAAGCCAACTTTGAGACAAATCATGCACCATTTC
481   ---------+---------+---------+---------+---------+---------+ 540
      ProLeuLysProIleValGluAsnAlaLysProThrLeuArgGlnIleMetHisHisPhe TCAGATGCAGCGGAAGCATATATTGAAATGAGAAACTCTGAAAGTCCGTATATGCCTAGA
541   ---------+---------+---------+---------+---------+---------+ 600
      SerAspAlaAlaGluAlaTyrIleGluMetArgAsnSerGluSerProTyrMetProArg TACGGATTACTGAGAAATTTGAGAGACAGGGAATTAGCACGCTATGCTTTTGACTTCTAT
601   ---------+---------+---------+---------+---------+---------+ 660
      TyrGlyLeuLeuArgAsnLeuArgAspArgGluLeuAlaArgTyrAlaPheAspPheTyr GAGGTTACTTCTAAAACGCCAAATAGGGCAAGAGAAGCAATAGCTCAAATGAAGGCCGCG
661   ---------+---------+---------+---------+---------+---------+ 720
      GluValThrSerLysThrProAsnArgAlaArgGluAlaIleAlaGlnMetLysAlaAla GCTCTCGCGGGAGTTAACAGCAGGTTATTTGGACTTGATGGTAATATCTCGACCAATTCC
721   ---------+---------+---------+---------+---------+---------+ 780
      AlaLeuAlaGlyValAsnSerArgLeuPheGlyLeuAspGlyAsnIleSerThrAsnSer
```

FIGURE 2B

```
      GAAAATACTGGGAGGCACACTGCAAGGGACGTAAATCAGAATATGCATACTTTGTTGGGT
781   ---------+---------+---------+---------+---------+---------+ 840
      GluAsnThrGlyArgHisThrAlaArgAspValAsnGlnAsnMetHisThrLeuLeuGly

ATGGGTCCACCGCAGTAAAGACTAGGTAAACTGGTCACAGTTAGCATTTCGGGTCGTTAT
841   ---------+---------+---------+---------+---------+---------+ 900
      MetGlyProProGlnEnd

AAGTTTTCTATAATATAACATGTCGCACTTTATTTTAGTATAGTGTGATTTCATCACCTT
901   ---------+---------+---------+---------+---------+---------+ 960

TGTACTGTTTATGTTAGCGTGGTTTAACCACCTTTGTGTGTGCTTTATATTATAGTTTAT
961   ---------+---------+---------+---------+---------+---------+ 1020

GCGTAGCAGGGAGAACCATTACAATGCCGGAGTTGTTTGTAGTGTGATTTCATCACGGTT
1021  ---------+---------+---------+---------+---------+---------+ 1080

AATAGCCGAGGTACGGTAATGTTTGTTGCCTAAAAAAAAAAAAAAAAAAAAAAAA
1081  ---------+---------+---------+---------+---------+-----    1135
```

FIGURE 3A

```
      ATGCTCCAATCAGGCACTCAACCAACTGTGGCAGACGCTAGAGTTACAAAGAAAGATAAA
  1   ---------+---------+---------+---------+---------+---------+   60
      MetLeuGlnSerGlyThrGlnProThrValAlaAspAlaArgValThrLysLysAspLys
                   ↑

GAAGATGACAAAGGGGAAAACAAGGATTTCACAGGCTCCGGCTCAGGTGAGAAAACAGTA
 61   ---------+---------+---------+---------+---------+---------+  120
      GluAspAspLysGlyGluAsnLysAspPheThrGlySerGlySerGlyGluLysThrVal

GTAGCTGCCAAGAAAGACAAGGATGTGAATGCTGGTTCTCATGGGAAAATTGTGCCGCGT
121   ---------+---------+---------+---------+---------+---------+  180
      ValAlaAlaLysLysAspLysAspValAsnAlaGlySerHisGlyLysIleValProArg

CTTTCGAAGATCACAAAGAAAATGTCATTGCCACGCGTGAAAGGGAATGTGATACTCGAT
181   ---------+---------+---------+---------+---------+---------+  240
      LeuSerLysIleThrLysLysMetSerLeuProArgValLysGlyAsnValIleLeuAsp

ATCGATCATTTGCTGGAATATAAGCCGGATCAAATTGAGTTATACAACACACGAGCGTCT
241   ---------+---------+---------+---------+---------+---------+  300
      IleAspHisLeuLeuGluTyrLysProAspGlnIleGluLeuTyrAsnThrArgAlaSer

CATCAGCAATTTGCCTCTTGGTTCAACCAAGTTAAGACAGAATATGATCTGAATGATCAA
301   ---------+---------+---------+---------+---------+---------+  360
      HisGlnGlnPheAlaSerTrpPheAsnGlnValLysThrGluTyrAspLeuAsnAspGln

CAGATGGGAGTTGTGATGAACGGTTTCATGGTTTGGTGTATTGAAAATGGCACCTCACCT
361   ---------+---------+---------+---------+---------+---------+  420
      GlnMetGlyValValMetAsnGlyPheMetValTrpCysIleGluAsnGlyThrSerPro

GACATTAATGGAGTGTGGTTTATGATGGACGGAAATGAACAAGTTGAGTATCCTTTGAAA
421   ---------+---------+---------+---------+---------+---------+  480
      AspIleAsnGlyValTrpPheMetMetAspGlyAsnGluGlnValGluTyrProLeuLys

CCGATAGTTGAAAATGCAAAGCCAACGCTGCGGCAAATAATGCATCATTTTTCAGATGCA
481   ---------+---------+---------+---------+---------+---------+  540
      ProIleValGluAsnAlaLysProThrLeuArgGlnIleMetHisHisPheSerAspAla

GCGGAGGCATATATAGAGATGAGAAATGCAGAGGCACCATACATGCCGAGGTATGGTTTG
541   ---------+---------+---------+---------+---------+---------+  600
      AlaGluAlaTyrIleGluMetArgAsnAlaGluAlaProTyrMetProArgTyrGlyLeu
```

FIGURE 3B

```
       CTTCGAAACCTACGGGATAGGAGTTTAGCACGATACGCTTTCGATTTCTATGAAGTCAAT
601    ---------+---------+---------+---------+---------+---------+  660
       LeuArgAsnLeuArgAspArgSerLeuAlaArgTyrAlaPheAspPheTyrGluValAsn

TCTAAAACTCCTGAAAGAGCCCATGAAGCTGTTGCGCAGATGAAAGCAGCAGCTCTTAGC
661    ---------+---------+---------+---------+---------+---------+  720
       SerLysThrProGluArgAlaHisGluAlaValAlaGlnMetLysAlaAlaAlaLeuSer

AATGTTTCTTCAAGTGTGTTTGGCCTTAGTGAAATCGTTGCCACCACTAGCGAAGCCACA
721    ---------+---------+---------+---------+---------+---------+  780
       AsnValSerSerSerValPheGlyLeuSerGluIleValAlaThrThrSerGluAlaThr

CTGAACGGCACACTGCACGTGATGTTAATAGAAACATGCCACACCTTACTAGGTGTGAAT
781    ---------+---------+---------+---------+---------+---------+  840
       LeuAsnGlyThrLeuHisValMetLeuIleGluThrCysHisThrLeuLeuGlyValAsn

ACAATGCAGTAAAGGGTAGGCCGCCTACCTAGGTTATCGCTTCGCTGCCGACGTAATTCT
841    ---------+---------+---------+---------+---------+---------+  900
       ThrMetGlnEnd

AATATTTACCAGCTTTATTTGATATCTTTAGATTTCCAGAGTGGGCCTCCCACCTTTAAA
901    ---------+---------+---------+---------+---------+---------+  960

GCGTAGAGTTTATGCTTAGTTGTCCAGGAGTGCCGTAGTCCTGTCGGAAGCTTTAGTGTG
961    ---------+---------+---------+---------+---------+---------+  1020

AGCCTCTCACGAATAAGCTCGAGATTAGACTCCGTTTGCAAGCCTAAAAAAAAAAAAAAA
1021   ---------+---------+---------+---------+---------+---------+  1080

AAAA
1081   ----  1084
```

FIGURE 4A

```
PRV-p   CAGTCCAAGAATGAAGCTGTGGATGCTGGTTTGAATGAAAAACTCAAAGA   50
        |||||||| ||||||||||||||| ||||||||||||||||| |||||||
PRV-w   CAGTCCAAAAATGAAGCTGTGGATACTGGTTTGAATGAAAAATTCAAAGA   50

GAAGGAAAATCAGAAAGAAAAAGAAAAAGAAAAACAAAAAGAGAAAGAAA  100
         |||||||| ||||||||||||||||||||||||||||||||||||||||
        AAAGGAAAAACAGAAAGAAAAAGAAAAAGAAAAACAAAAAGAGAAAGAAA  100

AAGACGGTGCTAGTGACGGAAATGATGTGTCAACTAGCACAAAAACTGGA  150
        |||||| |||||||||||||||||||||||||||||||||||||||||||
        AAGACGATGCTAGTGACGGAAATGATGTGTCAACTAGCACAAAAACTGGA  150

GAGAGAGATAGAGATGTCAATGTTGGGACCAGTGGAACTTTCACTGTTCC  200
        ||||||||||||||||||||||||||||||||||||||||||||||||||
        GAGAGAGATAGAGATGTCAATGTTGGGACCAGTGGAACTTTCACTGTTCC  200

GAGAATTAAATCATTTACTGATAAGATGGTTCTACCGAGAATTAAGGGGA  250
        |||||||||||||||||||||||||||| ||||||||||||||||||| |
        GAGAATTAAATCATTTACTGATAAGATGATTCTACCGAGAATTAAGGGAA  250

AGACTGTCCTTAATTTAAATCATCTTCTTCAGTACAATCCGCAACAAATT  300
        || ||||||||||||||||||| || |||||||| |||||||||||||||
        AGTCTGTCCTTAATTTAAATCACCTACTTCAGTATAATCCGCAACAAATT  300

GACATTTCTAACACTCGTGCCACTCATTCACAATTTGAGAAGTGGTATGA  350
        |||||||||||||||||||||||||| |||||||||||||||||||||||
        GACATTTCTAACACTCGTGCCACTCAGTCACAATTTGAGAAGTGGTATGA  350

GGGAGTGAGGAATGATTATGGCCTTAATGATAATGAAATGCAAGTGATGC  400
        ||||||||||||||||||||||||||||||||||||||||||||||||||
        GGGAGTGAGGAATGATTATGGCCTTAATGATAATGAAATGCAAGTGATGC  400

TAAATGGTTTGATGGTTTGGTGTATCGAGAATGGTACATCTCCAGACATA  450
        ||||||||||||||||||||||||||||||||||||||||||||||||||
        TAAATGGTTTGATGGTTTGGTGTATCGAGAATGGTACATCTCCAGACATA  450
```

FIGURE 4B

```
TCTGGTGTCTGGGTTATGATGGATGGGGAAACCCAAGTTGATTATCCAAT   500
||||||||||||||||||||||||||||||||||||||||||||||||||
TCTGGTGTCTGGGTTATGATGGATGGGGAAACCCAAGTTGATTATCCAAT   500

CAAGCCTTTGATTGAGCATGCTACTCCGTCATTTAGGCAAATTATGGCTC   550
|||||||| |||||||||||||||||||||||||||||||||||||||||
CAAGCCTTTAATTGAGCATGCTACTCCGTCATTTAGGCAAATTATGGCTC   550

ACTTTAGTAACGCGGCAGAAGCATACATTGCGAAGAGAAATGCTACTGAG   600
||||||||||| |||||||||||||||||||||| |||||||||||||||
ACTTTAGTAACGAGGCAGAAGCATACATTGCGAAAAGAAATGCTACTGAG   600

AGGTACATGCCGCGGTATGGAATCAAGAGAAATTTGACTGACATTAGCCT   650
||||||||||||||||||||||||||||||||||||||||||||||||||
AGGTACATGCCGCGGTATGGAATCAAGAGAAATTTGACTGACATTAGCCT   650

CGCTAGATACGCTTTCGACTTCTATGAGGTGAATTCGAAAACACCTGATA   700
||||||||||||||||||||||||||||||||||||||||||||||||||
CGCTAGATACGCTTTCGACTTCTATGAGGTGAATTCGAAAACACCTGATA   700

GGGCTCGCGAAGCTCACATGCAGATGAAGGCTGCAGCGCTGCGAAACACC   750
|||||||||||| |||||||||||||||||||||||| |||||||||||
GGGCTCGCGAAGCCCACATGCAGATGAAGGCTGCAGCACTGCGAAACACT   750

AGTCGCAAAATGTTTGGTATGGACGGCAGTGTTAGTAACAAGGAAGAAAA   800
||||||| ||||||||||||||||||||||||||||||||||||||||||
AGTCGCAGAATGTTTGGTATGGACGGCAGTGTTAGTAACAAGGAAGAAAA   800

CACGGAGAGACACACAGTGGAAGATGTCAATAGAGACATGCACTCTCTCC   850
||||||||||||||||||||||||| ||||||||||||||||||||||||
CACGGAGAGACACACAGTGGAAGACGTCAATAGAGACATGCACTCTCTCC   850

TGGGTATGCGCAACTAA   867
|||||||||||||||||
TGGGTATGCGCAACTAA   867
```

FIG. 5

```
SMV    SGKEKEGDMDADKDPKKSTSSSKG...............AGTSSKDVNV    34
       ||||  |||||||||| ||  |                  || ||||||
WMVII  SGKETVENLDAGKESKKDASDKGNKPQNSQVGQGSKEPTKTGTVSKDVNV    50

SMV    GSKGKVVPRLQKITRKMNLPMVEGKIILSLDHLLEYKPNQVDLFNTRATR    84
       |||||  |||||||||||||| |||||||||||||||||  ||||||||||
WMVII  GSKGKEVPRLQKITKKMNLPTVGGKIILSLDHLLEYKPSQVDLFNTRATK    100

SMV    TQFEAWYNAVKDEYELDDEQMGVVMNGFMVWCIDNGTSPDANGVWVMMDG    134
       ||||  || ||| ||||||||||| ||||||||||||||| ||| ||||||
WMVII  TQFESWYSAVKVEYDLNDEQMGVIMNGFMVWCIDNGTSPDVNGVMVMMDG    150

SMV    EEQIEYPLKPIVENAKPTLRQIMHHFSDAAEAYIEMRNSESOYMPRYGLL    184
       ||| ||||||||||||||||||||||||||||||||||||||| |||||||
WMVII  EEQVEYPLKPIVENAKPTLRQIMHHFSDAAEAYIEMRNSESPYMPRYGLL    200

SMV    RNLRDRELARYAFDFYEVTSKTPNRAREAIAQMKAAALSGVNNKLFGLDG    234
       |||||||||||||||||||||||||||||||||||||||| ||| |||||||
WMVII  RNLRDRELARYAFDFYEVTSKTPNRAREAIAQMKAAALAGVNSRLFGLDG    250

SMV    NISTNSENTERHTARDVNQNMHTLLGMGPPQ    265
       |||||||||| ||||||||||||||||||||
WMVII  NISTNSENTGRHTARDVNQNMHTLLGMGPPQ    281
``` pGA482/GG/cpZYMV

POTYVIRUS COAT PROTEIN GENES AND PLANTS TRANSFORMED THEREWITH

The present application is a continuation of U.S. Ser. No. 08/232,846, filed Apr. 25, 1994, now abandoned which is a continuation of U.S. Ser. No. 08/013,971, filed Feb. 4, 1993, now abandoned which is a continuation of U.S. Ser. No. 07/656,167, filed Feb. 19, 1991, now abandoned, which is a continuation of international application PCT/US89/03094, filed Jul. 20, 1989, which is a continuation of U.S. Ser. No. 07/368,710, filed Jun. 19, 1989, now abandoned, which is a continuation in part of U.S. Ser. No. 07/234,412, filed Aug. 19, 1988, and a continuation of U.S. Ser. No. 07/323,536, filed Mar. 14, 1989, each now abandoned.

FIELD OF THE INVENTION

The present invention relates to the coat protein genes of potyviruses. More specifically the invention relates to a process for preparing a coat protein gene from a potyvirus as well as its incorporation into a transfer vector, and its use in producing transformed plant cells and transformed plants which are resistant to viral infections by the particular potyvirus and related viruses from which the gene is derived.

BACKGROUND OF THE INVENTION

Potyviruses are a distinct group of plant viruses which are pathogenic to various crops. Potyviruses include watermelon mosaic virus II (WMVII); papaya ringspot virus strains papaya ringspot and watermelon mosaic I(PRV-p and PRV-w), two closely related members of the plant potyvirus group which were at one time classified as distinct virus types, but are presently classified as different strains of the same virus; zucchini yellow mosaic virus (ZYMV); and many others. These viruses consist of flexous, filamentous particles of dimensions approximately 780×12 nanometers. The viral particles contain a single-stranded RNA genome containing about 10,000 nucleotides of positive (+, coding, or sense) polarity. Translation of the RNA genome of potyviruses shows that the RNA encodes a single large polyprotein of about 330 kD. The polyprotein contains several proteins, one of which is a 49 kD protease that is specific for the cleavage of the polyprotein into at least six (6) other peptides. One of the proteins contained within this polyprotein is a 35kD capsid or coat protein which coats and protects the viral RNA from degradation.

The genome organization of several viruses belonging to the potyvirus family group has been studied in detail, in particular tobacco etch virus, tobacco vein mottling virus and pepper mottle virus. In each case, the location of the coat protein gene has been at the 3'-end of the RNA, just prior to a stretch of 200 to 300 bases) terminal adenine nucleotides residues. The location of the 49 kD protease gene appears to be conserved in these viruses. In the tobacco etch virus, the protease cleavage site has been determined to be the dipeptide Gln-Ser, Gln-Gly or Gln-Ala. Conversation of these dipeptides as the cleavage sites in these viral polyproteins is apparent from the sequences of the above-listed potyviruses.

Expression of the coat protein genes from tobacco mosaic virus, alfalfa mosaic virus, cucumber mosaic virus, and potato virus X in transgenic plants has resulted in plants which are resistant to infection by the respective virus. In order to produce such transgenic plants, the coat protein gene must be inserted into the genome of the plant. Furthermore, the coat protein gene must contain all the genetic control sequences necessary for the expression of the gene after it has been incorporated into the plant genome.

Since the coat protein of a potyvirus is produced by the post translation processing of a polyprotein, the coat protein gene isolated from viral RNA does not contain the genetic regulatory sequences needed for gene expression. The coat protein gene does not contain the transcription and translation signals necessary for its expression once transferred and integrated into a plant genome. It must, therefore, be engineered to contain a plant expressible promoter, a translation initiation codon (ATG) and a plant functional poly(A) addition signal (AATAAA) 3' of its translation termination codon.

In the present invention, the nucleotide sequences of the cat protein genes for WMV-II, PRV-p and ZYMV have been determined, and the genes have been inserted into expression vectors to supply them with the necessary genetic regulatory sequences so that the genes can be expressed when incorporated into a plant genome. Plant cells are transformed with the vector construct and the plant cells are induced to regenerate. The resulting plants contain the coat protein genes and produce the coat protein. The production of the protein confers upon the plant an increased resistance to infection by the virus from which the coat protein gene was derived.

INFORMATION DISCLOSURE

European patent application EP 0 223 452 describes plants that are resistant to viral diseases and methods for producing them. The process described comprises the steps of transforming a plant with a DNA insert comprising a promoter, a DNA sequence derived from the virus, and a poly(A) addition sequence.

PCT patent application PCT/US86/00514 refers generally to a method of conferring resistance to a parasite to a host of the parasite.

Allison et al. (1985) "Biochemical Analysis of the Capsid Protein Gene and Capsid Protein of Tobacco Etch Virus: N-Terminal Amino Acids Are Located on the Virion's Surface", Virology 147:309–316, describe the nucleotide sequence at the 3' end of the tobacco etch virus genome encoding the capsid protein. Homology to the sequence encoding the capsid protein of Pepper mottle virus is reported.

Allison et al. (1986) "The Nucleotide Sequence of the Coding Region of Tobacco Etch Virus Genomic RNA: Evidence for the Synthesis of a Single Polyprotein", Virology 154:9–20 describe the genome organization of the tobacco etch virus.

Carrington, J. C. and Dougherty, W. G. (1987) "Small nuclear inclusion protein encoded by a plant potyvirus genome is a protease", J. Virology 61:2540–2548, disclose that the viral RNA of tobacco etch virus encodes the 49K protease responsible for cleavage of the polyprotein produced when the viral RNA is translated.

Dodds et al. (1985) "Cross Protection between strains of cucumber mosaic virus: effect of host and type of inoculum on accumulation of virions and double-stranded RNA of the challenge strain", Virology 144:301–309, describe increased resistance to challenge by virus conferred to a plant by infection of a different strain of virus.

Dougherty, W. G. et al. (1985) "Nucleotide Sequence at the 3' Terminus of Pepper Mottle Virus Genomic RNA: Evidene for an Alternative Mode of Potyvirus Capside Protein Gene Organization", Virology 146:282–291, report the nucleotide sequence of the 3' terminus of the viral RNA genome of pepper mottle virus.

Dougherty, W. G. et al. (1988) "Biochemical and mutational analysis of plant virus polyprotein cleavage site", EMBO J. 7:1281–1287, describe the conservation of the proteolytic cleave site among geographically distinct isolates of tobacco each virus.

Dougherty, W. G. and Carrington, J. C. (1988) "Expression and function of potyviral gene products", Ann. Rev. Phytopathol. 26:123–143, describe potyviruses and some of the similarities the members of the group have with each another.

Eggenberger, A. L. et al. (1989) "The nucleotide sequence of a Soybean Mosaic Virus Coat Region region and its expression in *Escherichia coli, Agrobacterium tumefaciens,* and tobacco callus", Virology, in press, disclose the nucleotide sequence of the coat protein gene for soy bean mosaic virus.

Hinchee, M. A. W. et al (1988) "Production of transgenic soybean plants using Agrobacterium-mediated DNA transfer", Bio/tech. 6:915–921, disclose the production of transgenic soybean plants which were transformed with *A. tumerfacien* plasmids that conferred either Kanamycin resistance/β-glucuronidase activity or Kanamycin resistance/glyphosphate tolerance.

Kozak, M. 1986) "Point mutations define a sequence flanking the AUG initiator codon that modulates translation by eukaryotic ribo-somes", Cell 44:283–292, discloses the optimal sequence around the ATG initiator codon of the preproinsulin gene for initiation by eukaryotic ribosomes.

Loesch-Fries et al. (1987) "Expression of alfalfa mosaic virus RNA 4 in transgenic plants confers virus resistance", EMBO J 6:1845–1851, disclose that expression of the coat protein gene of alfalfa mosaic virus in transgenic plants confers resistance to infection by the virus.

Pietrzak et al. (1986) "Expression in plants of two bacterial antibiotic resistant genes after protoplast transformation with a new plant expression vector", Nucleic Acids Research 14,5857–5868, dis-close expression in plants of foreign genes introduced into the plant using an expression vector containing a movable expression cassette consisting of the Cauliflower mosaic virus 35S promotor and transcription terminator separated by a polylinker containing several unique restriction sites.

Powell-Abel et al. (1986) "Delay of disease development in transgenic plants that express the tobacco mosaic virus coat protein gene", Science 232:738–743, disclose increased resistance toward infection by tobacco mosaic virus in transgenic plants containing the coat protein gene from tobacco mosaic virus.

Quemada, H. D. et al. (1989) "The nucelotide sequences of cDNA clones from RNA3 of Cucumber Mosaic Virus strains C and WL", J. Gen Virol. 70:1065–1073, reports the nucleotide sequences of cDNA clones from RNA3 of Cucumber Mosaic Virus strains C and WL and compares them to each other and other strains for homolgy.

Shukla, D. D. et al. 1986) "Coat Proteins of Potyviruses", Virology 152:118–125, discloses the amino acid sequence of the potato virus Y coat protein.

Shukla, D. D. et al. (1988) "The N and C termini of the Coat Proteins of Potyviruses Are Surface-located and the N Terminus Contains the major Virus-specific Epitopes", J. Gen Virol. 69:1497–1508, disclose that the N- and C-termini regions of some potyvirus coat proteins are located at the surface of the viral particles. The viral particles were treated with trypsin and it was observed that the enzyme treatment removed 30–67 amino acids from the N-terminal and 18–20 amino acids from the C-terminal; the variations were dependent on the virus. The remaining portion of the coat protein, the core, was highly conserved among the various viruses.

Tumer et al. (1987) "Expression of alfalfa mosaic virus coat protein gene confers cross-protection in transgenic tobacco and tomato plants", EMBO J. 6:1181–1188, disclose transgenic tobacco and tomato plants transformed with the coat protein gene of alfalfa mosaic virus displayed increased resistance to infection by alfalfa mosaic virus.

Yeh and Gonsalves (1985) "Translation of Papaya Ringspot Virus RNA in vitro: Detection of a Possible Polyprotein That is Processed for Capsid Protein, Cylindrical-Inclusion Protein, and Amor-phous-Inclusion Protein", Virology 143:260–271, describe the possibility that the RNA genome encodes a single proprotein which undergoes post-translational processing to form the potyvirus protein products.

The following scientific publications are of interest but not relevant:

An et al. (1985) "New cloning vehicles for transformation of higher plants", EMBO J. 4:277–285 describe the construction of an expression plasmid which may be stably replicated in both *E. coli* and *A. tumerfaciens.*

An, G. (1986) "Development of plant promoter expression vectors and their use for analysis of differential activity of nopaline synthase promoter in transformed tobacco cells", Plant Physiol. 81:86–91, reports differences in promoter activities of transferred genes within the same cells as well as in independently derived cell lines.

Bevan et al. (1983) "Structure and transcription of the nopaline synthase gene region of T-DNA", Nucleic Acids Research 11:369–385, disclose the DNA sequence and plant-tumor transcription pattern of a portion of DNA from *A. tumerfaciens* strain T37.

Depicker et al. (1982) "Nopaline synthase: transcript mapping and DNA sequence", J. Mol. Appl. Genet. 1:561–573, disclose the DNA sequences 5' and 3' to the nos gene found in *A. tumerfaciens.*

Hepburn, A. et al. (1985) "The use of pNJ5000 as an intermediate vector for genetic manipulation of Agrobacterium Ti-plasmids", J. General Microbio. 131:2961–2969, describe vectors which are used to transfer narrow host range vectors from *E. coli* to *A. tumerfaciens.*

Klein et al., (1987) "High-velocity microprojectiles for delivering nucleic acids into living cells", Nature 327:70–73, disclose that nucleic acids may be delivered into living cells using accelerated, small tungsten balls which pierce the cells without killing them.

Klein et al., (1988) "Factors influencing gene delivery into *Zea mays* cells by high-velocity microprojectiles", Bio/tech. 6:559–563, disclose that two days after bombarding plant cells with a plasmid coated microprojectile, expression of an gene encoding an enzyme could be detected.

Mazur, B. J. and Chui, C.-F. (1985) "Sequence of a genomic DNA clone for the small subunit of ribulose bis-phosphate carboxylase-oxygenase from tobacco", Nucleic Acids Research 13:2373–2386, disclose the DNA sequence of the small subunit of ribulose bis-phosphate carboxylase-oxygenase from tobacco.

McCabe, D. E., et al., (1988) "Stable transformation of soybean (Glycine max) by particle acceleration", Bio/tech. 6:923–926, disclose expression in soybean shoots of foreign genes introduced into immature soybean seeds using DNA coated microprojectiles.

Olson M. K. et al (1989) "Enhancement of heterologous polypeptide expression by alterations in the ribosome-binding-site sequence", J. Biotech. 9:179–190, discloses the increase in gene expression of heterologous genes in *E. coli* due to the presence of an AT-rich 5' untranslated region.

Slightom et al. (1983) "Complete nucleotide sequence of a French bean storage protein gene: Phaseolin", Proc. Natl. Acad. Sci. U.S.A. 80:1897–1901, disclose the complete nucleotide sequences of the gene and the mRNA coding for a specific phaselin type French bean major storage protein.

Vilaine, F. and Casse-Delbart, F. (1987) "Independent induction of transformed roots by the TL and TR regions of the Ri plasmid of agropine type Agrobacterium rhizogenes", Mol. Gen. Genet. 206:17–23, disclose the respective role of Tl- and TR-DNA in root induction by agropine type Agrobacterium rhizogenes Ri plasmids.

None of these documents, either alone or taken together, teaches or suggests the instant invention which relates to potyvirus coat protein genes and plants transformed therewith.

SUMMARY OF THE INVENTION

The present invention relates to the coat protein genes of Papaya Ringspot Virus Strain papaya ringspot (PRV-p), Watermelon Mosaic Virus II(WMVII), and Zucchini Yellow Mosaic Virus (ZYMV).

The present invention relates to a recombinant DNA molecule which encodes a potyvirus coat protein. The present invention relates to a recombinant DNA molecule comprising a potyvirus coat protein gene operably linked to genetic regulatory sequences necessary for gene expression.

The present invention relates to expression vectors which contain a coat protein gene for potyviruses, and additionally, the necessary genetic regulatory sequences needed for expression of a gene transferred into a plant. The present invention also relates to bacterial or plant cells which are transformed with an expression vector containing the coat protein genes. Furthermore, the present invention relates to transgenic pants which are produced from plant cells transformed with an expression vector containing the coat protein gene for potyviruses. In addition, the present invention relates to a process of producing transgenic plants which have increased resistance to viral infection.

BRIEF DESCRIPTION OF THE DRAWINGS

FIGS. 1A–1B show the sequence of the PRV-p coat protein gene and protein.

FIGS. 2A–2B show the WMVII coat protein gene and protein.

FIGS. 3A–3B show the ZYMV coat protein gene and protein.

FIGS. 4A–4B show a comparison of the PRV-p coat protein gne with the virus PRV-w.

FIG. 5 shows a comparison of the WMVII coat protein gene with Soybean Mosaic virus strain N.

Figure 6:
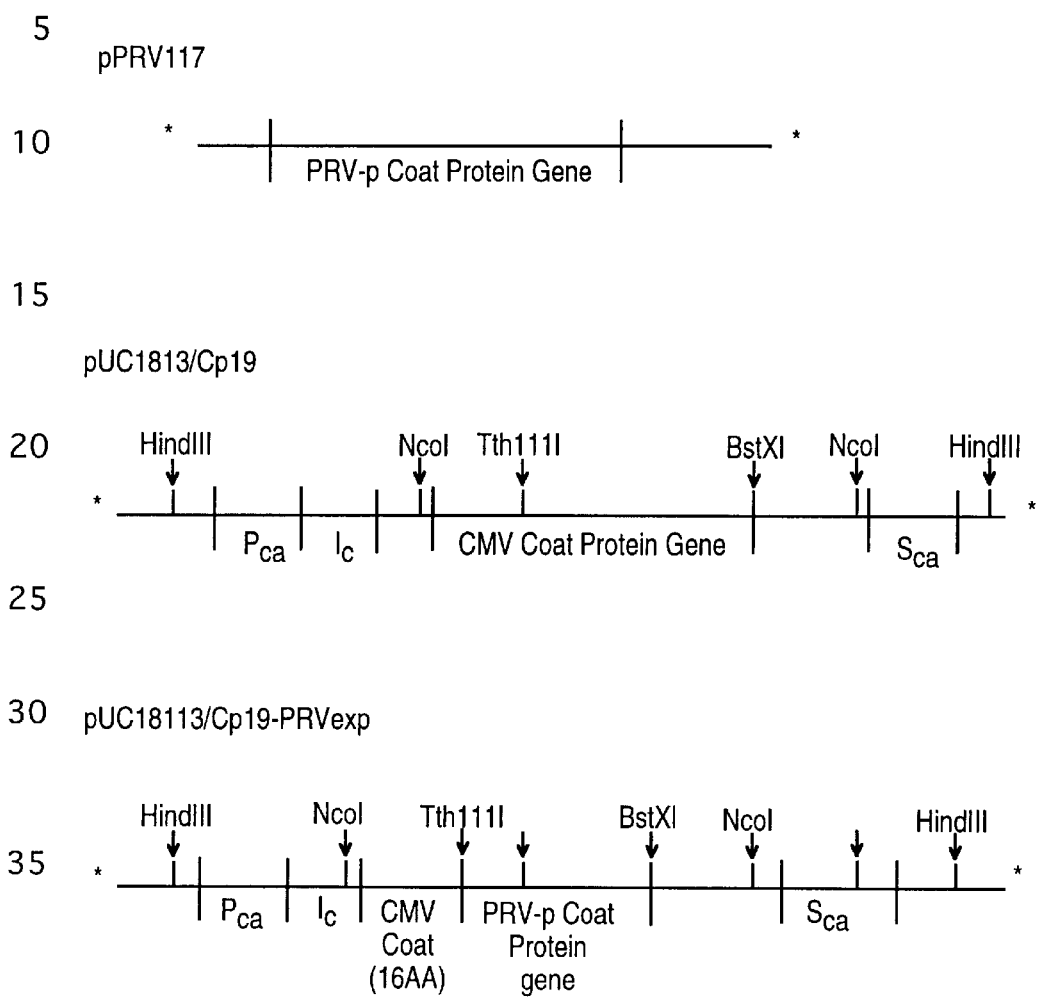
FIG. 6 shows the construction of pUC1813/CP19-PRVexp.

Certain conventions are used to illustrate plasmids and DNA fragments as follows:

(1) The single line figures represent both circular and linear double-stranded DNA.

(2) Asterisks (*) indicate that the molecule represented is circular. Lack of an asterisk indicates the molecule is linear.

(3) Junctions between natural boundaries of functional components are indicated by vertical lines along the horizontal lines.

(4) Genes or functional components are indicated below the horizontal lines.

(5) Restriction sites are indicated above the horizontal lines.

(6) Distances between genes and restriction sites are not to scale. The figures show the relative positions only unless indicated otherwise.

(7) The following abbreviations are used to denote function and components:
 a) $P_{ca}$=CaMV35S promotor;
 b) $I_c$=CMV intergenic region, the intergenic region comprising the initiation codon and AT rich 5' untranslated region;
 c) $S_{ca}$=CaMV35S poly(A) addition signal; and
 d) Nos=Nos nptII gene.

DETAILED DESCRIPTION OF THE INVENTION

Most of the recombinant DNA methods employed in practicing the present invention are standard procedures, well known to those skilled in the art, and described in detail in, for example, Eurpean Patent Application Publication Number 223452, published Nov. 29, 1986, which is incorporated herein by reference. Enzymes are obtained from commercial sources and are used according to the vendor's recommendations or other variations known in the art. General references containing such standard techniques include the following: R. Wu, ed. (1979) Methods in Enzymology, Vol. 68; J. H. Miller (1972) Experiments in Molecular Genetics; T. Maniatis et al. (1982) Molecular Cloning: A Laboratory Manual; D. M. Glover, ed. (1985) DNA Cloning Vol. II; H. G. Polites and K. R. Marotti (1987) "A step-wise protocol for cDNA synthesis". Biotechniques 4:514–520; S. B. Gelvin and R. A. Schilperoort, eds. Introduction, Expression, and Analysis of Gene Products in Plants, all of which are incorporated by reference.

For the purposes of the present disclosure the following definitions apply.

"Promotor" means a promoter which is functional in the host plant.

"Initiation region" includes the initiation codon and nucleotides flanking the initiation codon.

"Operably linked" refers to the linking of nucleotide regions encoding specific genetic information such that the nucleotide regions are contiguous, the functionality of the region is preserved and will perform its function relative the the other regions as part of a functional unit.

"AT rich 5' untranslated region" is a nucleotide sequence composed of at least 60% adenine or thiamine nucleotides.

"Untranslated flanking region" refers to nucleotide sequences which are 3' of the termination codon and end at the poly(A) addition signal. These sequences enhance production of the peptide encoded by the upstream gene.

"Vector" is a vehicle by means of which DNA fragments can be introduced into host organisms.

"Expression vector" is a vehicle by means of which DNA fragments that contain sufficient genetic information and can, therefore, be expressed by the host, can be introduced into host organisms.

"Antipathogen gene" is a gene which encodes a DNA sequence which is either the antisense sequence of a pathogenic gene or the antipathogenic gene encodes a peptide whose presence in an organisms confers an increased resistence to a pathogen.

To practice the present invention, the coat protein gene of a virus must be isolated from the viral genome and inserted into a vector containing the genetic regulatory sequences necessary to express the inserted gene. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different courses exist to isolate the coat protein gene. To do so, one having ordinary skill in the art can use information about the genome organization of potyviruses to locate and isolate the coat protein gene. The coat protein gene is located at the 3' end of the RNA, just prior to a stretch of about 20–300 adenine nucleotide residues. Additionally, the information relates to proteolytic cleavage sites is used to determine the N-terminus of the potyvirus coat protein gene. The protease recognition sites are conserved in the potyviruses and have been determined to be either the dipeptide Gln-Ser, Gln-Gly or Gln-Ala. The nucleotide sequence which encode these dipeptides can be determined.

Using methods well known in the art, a quantity of virus is grown up and harvested. The viral RNA is then separated and the coat protein gene can be isolated using a number of known procedures. A cDNA library is created using the viral RNA. The methods followed to do this are well known in the art. The viral RNA is treated with reverse transcriptase and a complementary DNA molecule is produced. A DNA complement of the complementary DNA molecule is produced and that sequence represents a DNA copy of the original viral RNA molecule. Thus, a double stranded DNA molecule is generated which contains the sequence information of the viral RNA. These DNA molecules can be closed in *E. coli* plasmid vectors after the additions of restriction enzyme linker molecules by DNA ligase. The various fragments are inserted into cloning vectors which are then used to transform *E. coli* and create a cDNA library.

Since the coat protein gene is located just 5' to the polyA region, oligonucleotides that can hybridize to the polyA region can be used as hybridization probes to screen the cDNA library and determine if any of the transformed bacteria contain DNA fragments with sequences coding for the polyA region. The cDNA inserts in any bacterial colonies which contain this region can be sequenced. The coat protein gene is present in its entirety in colonies which have sequences that extend 5' to the sequence which encodes the proteo-lytic cleavage site described above.

Alternatively, cDNA fragments may be inserted into expression vectors. Antibodies against the coat protein may be used to screen the cDNA expression library and the gene can be isolated from colonies which express the protein.

Using the sequences disclosed in FIGS. 1A–1B, 2A–2B and 3A–3B, the coat protein genes for the respective viruses may be synthesized chemically by methods well known in the art. Alternatively, the information in FIGS. 1A–1B, 2A–2B and 3A–3B may be used to synthesize oligonucleotides which can be used as probes to screen a cDNA library.

The nucleotide sequences of the coat protein genes for WMV-II, PRV-p and ZYMV have been determined and the genes have been inserted into expression vectors. The expression vectors contain the necessary genetic regulatory sequences for expression of an inserted gene. The coat protein gene is inserted such that those regulatory sequences are functional so that the genes can be expressed when incorporated into a plant genome.

In order to express the viral gene, the necessary genetic regulatory sequences must be provided. Since the coat protein of a potyvirus is produced by the post translational processing of a polyprotein, the coat protein gene isolated from viral RNA does not contain the genetic regulatory sequences needed for gene expression. The coat protein gene does not contain the transcription and translation signals necessary for its expression once transferred and integrated into a plant genome. It must, therefore, be engineered to contain a plant expressible promoter, a translation initiation codon (ATG) and a plant functional poly(A) addition signal (AATAAA) 3' of its translation termination codon. In the present invention, the coat protein is inserted into a vector which contains a cloning site for insertion 3' of the initiation codon and 5' of the poly(A) signal. The promoter is 5' of the initiation codon such that when a structural gene is inserted at the cloning site, a functional unit is formed in which the inserted gene is expressed under the control of the various genetic regulatory sequences.

In the preferred embodiment of the present invention, additional genetic regulatory sequences are provided. As described above, an expression vector must contain a promoter, an initiation codon and a poly(A) addition signal. In order to get a higher level of expression, untranslated regions 5' and 3' to the inserted genes are provided. Furthermore, certain sequences flanking the initiation codon optimize expression. The promoter used is one that is chosen for high level expression.

A 5' untranslated region which results in higher level expres-sion of an inserted gene is provided downstream from the promoter and upstream from the initiation codon. This region contains at least 60% of the sequence a Adenine and Thymine. There is a statistical bias for expression when such an AT rich region is located between the promoter and initiation codon. This preference is utilized in the preferred embodiment of the present invention by inclusion of an AT rich 5' untranslated region intermediate of the promoter and initi-ation codon.

The preferred embodiment of the present invention also contains specific nucleotide sequence flanking the initiation codon. This preferred sequence, termed Kozak's element, is AAXXATGG wherein X represents any of the four nucleotides. The presence of the initiation codon following Kozak's rule results in higher level expression when used in an expression vector. In the preferred embodiment of the present invention, the small subunit from the SS RUBISCO contains an initiation codon in which Kozak's element is used.

Furthermore, the preferred embodiment of the present invention contains a 3' untranslated region downstream from the cloning site where the coat protein gene is inserted and upstream from the poly(A) addition signal. The sequence of this 3' untranslated region results in a statistical bias for protein production. The sequence promotes high level expression. The poly(A) addition signal is found directly downstream from the 3' untranslated region and can be derived from the same source. In the preferred embodiment of the present invention, the 3' untranslated region and poly(A) addition signal are derived from CaMV 35S gene or the phaseolin seed storage protein gene.

The poly(A) addition signal from CaMV, nopaline synthase, octopine synthase, bean storage protein, and SS RUBISCO genes are also suitable for this construction. Several promoters which function in plants are available, but the best promoters are the constitutive promoter from cauliflower mosaic virus (CaMV, a plant DNA virus) and the small subunit of ribulose bis-phosphate carboxylase-oxygenase (SS RUBISCO) gene.

Using methods well known to those skilled in the art, plant cells are transformed with the vector construct and the plant cells are induced to regenerate. The resulting plants contain the coat protein genes ad produce the coat protein. The production of the protein confers upon the plant an increased resistance to infection by the virus from which the coat protein gene was derived.

DESCRIPTION OF THE PREFERRED EMBODIMENTS

EXAMPLE 1

Isolation of WMVII RNA

Watermelon mosaic virus II (WMV II) was propagated in zucchini squash (*Cucurbita pepo L*) plants and RNA was isolated by the method described by Yeh and Gonsalves (Virology 143:260, 1985).

EXAMPLE 2

Isolation of PRV-p RNA

Papaya ringspot virus strain prv (PRV-p) was propagated in jelly melon. *Cucumis metuliferus* (Nand.) Mey. Acc. 2549 plants and RNA was isolated by the method described by Yeh and Gonsalves (Virology 143:260, 1985).

EXAMPLE 3

Isolation of ZYMV RNA zucchini yellow mosaic (ZYMV) was propagated in zucchini squash (*Cucurbita pepo L*) plants and RNA was isolated by the method described by Yeh and Gonsalves (Virology 143:260, 1985).

EXAMPLE 4

Synthesis of double-stranded cDNA

The procedure used to make double stranded cDNA from isolated viral RNA is the same for all viral RNA isolated above. The purified RNA was subjected to the cDNA synthesis proptocal described by Polites and Marotti (Biotechniques 4:514, 1986) and because this RNA contains an A-rich region at its 3'-end (similar to that found for many eukaryotoic mRNAs) the procedure was straight-forward. The synthesis of double stranded cDNA was also done as described by Polites and Marotti. After double-stranded cDNA was synthesized, it was purified by passage through a G-100 Sephadex column, precipitated with ethanol, and suspended in 20 µl of 10X EcoRI methylase buffer (100 mM NaCl, 100 mM Tris-HCl, pH 8.0, 1 mM EDTA, 80 µM S-adenosyl methionine, and 100 µg/ml bovine serum albumin). An additional amount of S-adenosyl methionine (1 µl of a 32 mM solution) was added to the reaction mixture, followed by the addition of 1 µl (20 units) EcoRI methylase. The reaction was incubated at 37° C. for 30 minutes and stopped by incubation at 70° C. for 10 minutes. Then 1 µl (5 units) of *E. coli* DNA polymerse I Klenow fragment was added and incubated at 37° C. for 10 minutes, followed by phenol/chloroform extraction and ethanol precipitation. The pellet was washed in 70% ethanol, then 70% ethanol/0.3M sodium acetate. The pellet was dried and resuspendedin 8 µl of 0.5 µg/µl posphorylated EcoRi linkers (Collaborative Research Inc., 128 Spring St., Lexington, Mass. 02173). One µl of 10X ligas buffer (800 mM Tris-Hcl ph 8.0, 200 mM MgCl$_2$. 150 mM DTT, 10 mM ATP) and 1 µl of T4 DNA ligase (4 units) were added, and the reaction was incubated overnight at 15° C. The ligation reaction was stopped by incubation at 65° C. for 10 minutes. Sixty µl of H$_2$O, 10 µl of 10X EcoRI salts (900 mM Tris-HCl pH 8.0, 100 mM MgCl$_2$, 100 mM NaCl), and 10 µl of EcoRI (10 units/µl) were added, and the reaction was incubated at 37° C. for 1 hour. The reaction was stopped by phenol/chloroform and chloroform extractions. The reaction mixture was then size fractionated by passage through a Sephadex G-100 column and the fractions containing the largest double stranded cDNA molecules were concentrated by butanol extractions, precipitated with ethanol, and resuspended in 10 µl of H$_2$O. Five µl of the double stranded cDNAs was added to 0.5 µg of pUC19 DNA (which has been previously treated with phosphatase to remove the 5' phosphates), 1 µl of 10X ligase buffer, and 1 µl of T4 ligase, and the reaction was incubated at 15° C. for 16 hours. The resulting ligated pUC19-coat protein gene double stranded cDNA molecules were transformed into *E. coli* host cells as described by the manufacturer (Bethesda Research Laboratories, Inc., Gaithersburg, Md. 20877) and plated on medium containing 50 µg/ml ampicillin, 0.04 mM IPTG, and 0.004% X-Gal. Bacterial colonies showing no blue color were selected for further analysis. Clones containing the 3'-region and possibly the coat protein gene were identified by hybridization against a $^{32}$P-labeled oligo-dT. Bacterial colonies showing hybridization to this probe should contain at least the poly(A) region of the particular potyvirus genome. Several of the hybridizing bacterial clones were selected and plasmid DNAs were isolated according to methods known to those skilled in the art.

EXAMPLE 5

Identification of the PRV-p Coat Protein Gene

Several of the cloned cDNAs of PVP-p RNA were sequenced by the chemical DNA sequencing method described by Maxam and Gilbert (Methods of Enzymology 65:499, 1980). Based on this information and comparative analysis with other potyviruses clone number pPRV-117 was found to contain a complete copy of the PRV-p coat protein gene. The N-terminus of the coat protein was identified by the location of the dipeptide sequence Gln-Ser. The length of the PRV-p coat protein gene coding region is consistent with a gene encoding protein of about 33 kDal. The sequence of the PRV-p cot protein gene and protein are shown in FIGS. 1A-1B. In addition, comparison of this sequence with that of the related virus PRV-w described by Nagel and Heibert (Virology 143:435, 1985) shows that the two coat protein genes share 98% nucleotide and amino acid similarities FIGS. 4A-4B. Because these two viruses share extensive identities in their coat proteins, expression of the coat protein gene from PRV-p is expected to yield plants resistant to both PRV-p and PRV-w.

EXAMPLE 6

Construction of a Plant-expressible PRV-p Coat Protein Gene Cassette with CaMV 35S Promoter and Polyadenylation Signal and CMV 5' Untranslated Region and Translation Initiator ATG.

Attachment of the necessary plant regulatory signals to the PRV-p coat protein gene was accomplished by constructing a translational fusion with a clone originally designed for the expression of the CMV coat protein gene, using clone pUC1813/CP19. Plasmid pUC1813/CP19 is a vector suitable for agrobacterium mediated gene transfer. An EcoRI-EcoRI fragment was removed from pDH51/CP19 and placed into the EcoRI site of the plasmid, pUC1813 (available from Robert K., Department of Chemistry, Washington State University, Pullman, Wash.), created plasmid pUC1813/CP19. Plasmid pUC1813/CP19 was described in U.S. patent application Ser. No. 07/135,591 filed on Dec. 21, 1987 incorporated herein by reference. This trans-lational fusion clone was constructed by first identifying two restriction enzyme sites within clone pUC1813/CP19. One site (Tth111 I) is located between amino acids 13 to 17 while the other site (BstX I) is located near the end of the 3'-untranslated region of the CMV coat protein gene.

Addition of these specific restriction enzyme sites to the PRV-p coat protein gene was accomplished by the polymerase chain reaction technique, using an instrument and Taq polymerase purchased from Perkin Elmer-Cetus, Emeryville, Calif. Specifically, two respective 5' and 3' oligomers (CGACGTCGTCAGTCCAAGAATGAAGCTGTG, containing a Tth111 I site and (CCCACGAAAGTGGGGTGAAACAGGGTCGAGTCAG, containing a BstX I site), sharing at least 20 nucleotides with the PRV-p coat protein gene were used to prime synthesis and gene amplification of the coat protein gene. After synthesis, the amplified fragments were digested with Tth111 I and BstX I to expose the sites.

As shown in FIG. 6, pUC1813/CP19 is the expression vector which contains the CMV coat protein gene. Plasmid pUC1813/CP19 contains Tth111 I and BstX I sites.

The digested, amplified fragments are ligated into the respec-tive exposed sites of pUC1813/CP19 and the expected new construction was identified using methods known to those skilled in the art. Polymerase chain reaction techniques were used to amplify PRV-P coat protein gene containing the Tth111 I and BstXI sites. The plasmid pUC1813/CP19 and PRV-P coat protein gene fragments were digested with Tth111I and BstXI and ligated to each other. The resulting clone, designated pUC1813/CP19-PRVexp, was subjected to nucleotide sequencing to ensure that the cloning and gene amplification did not introduce any detrimental artifacts. The sequence showed no arti-facts, suggesting that this plant expression cassette should be capable of expressing a PRV-p coat protein gene which contains an additional 16 amino acids of CMV coat protein at its N-terminus.

EXAMPLE 7

Construction of a Micro T-DNA Plasmid Containing the Plant-expressible PRV-p Coat Protein Gene Construction.

Figure 7:
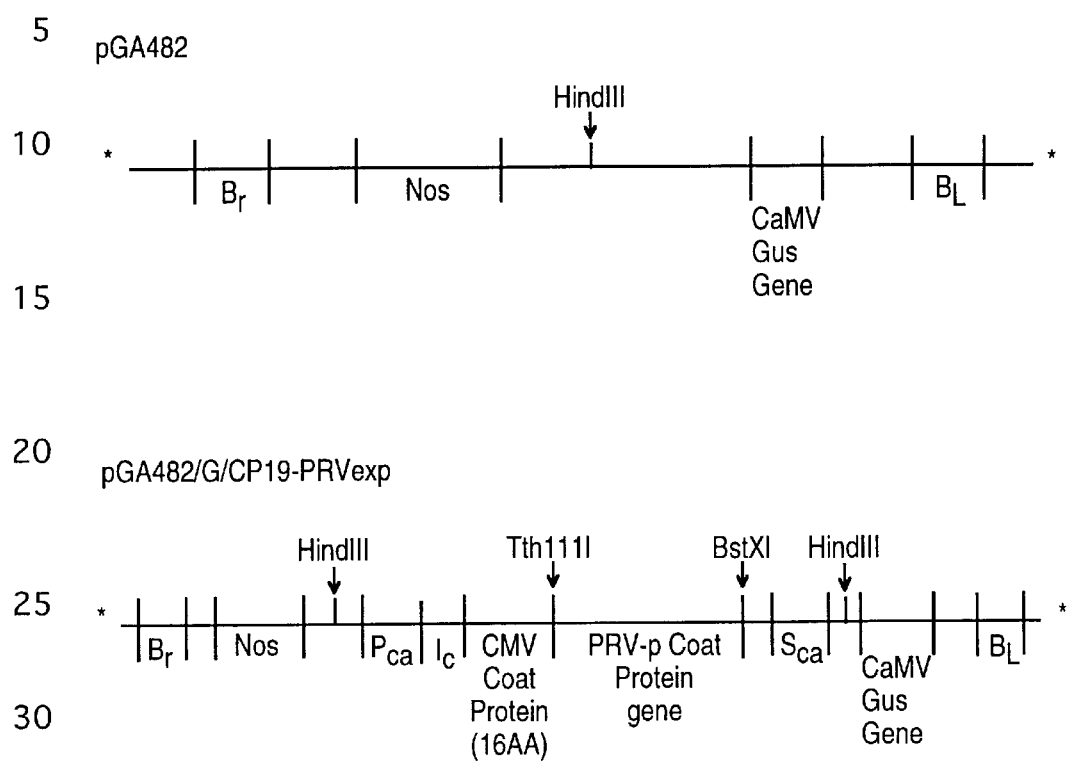
FIG. 7 shows the construction of pGA482/G/CP19-PRVexp.

As depicted in FIG. 7, the plant expression cassette for the PRV-p coat protein gene was transferred into a suitable micro T-DNA vector which contains the necessary Agrobacterium T-DNA transfer signals for transfer from an Agrobacterium and integration into a plant genome, and a wide host-range origin of replication (for replication in Agrobacterium). Plasmid pUC1813/CP19-PRV exp was digested with Hind III and the resulting 2.2 kb insert fragment containing the plant-expressible cassette was removed and ligated into the HIND III site of the modified Agrobacterium-derived micro-vector pGA482 (modification included the addition of the β-glucuronidase gene). The micro T-DNA vector, pGA482, is available from G. An, Institute of Biological Chemistry, Washington State University, Pullman, Wash. The resulting plasmid was designated, pGA482/G/CP19-PRVexp and is shown in FIG. 7. This plasmid (or derivatives thereof) was transferred into virulent or avirulent strains of *Agrobacterium tumefaciens* or rhizogenes, such as A208, C58, LBA4404, C58Z707, A4RS, A4RS(pRiB278b), and others. Strains A208 C58, LBA4404, and A4RS are available from American Type Culture Collection (ATCC), 12301 Parklawn Drive, Rockville, Md. Bacteria A4RS(pRiB278b)is available from Dr. F. Casse-Delbart, C.N.R.A., Routede Saint Cyr. F78000, Versailles, France. Strain C58Z707 is available from Dr. A. G. Hepburn, Dept. of Agronomy, University of Illinois, Urbana, Ill.

After transfer of the engineered plasmid pGA482/G/CP19-PRVexp into any of the above listed Agrobacterium strains, the Agro-bacterium strains can be used to transfer and integrate within a plant genome the plant-expressible PRV-p coat protein gene contained within its T-DNA region. This transfer can be accomplished using the standard methods for T-DNA transfers which are known to those skilled in the art, or this transfer can be accomplished using the methods described in a U.S. patent application Ser. No. 07/135,655, filed on Dec. 21, 1987, entitled "Agrobacterium Mediated Transformation of Germinating Plant Seeds" and incorporated herein by reference.

EXAMPLE 8

Construction of a Plant-expression Cassette for Expression of Various Genes in Transgenic Plants.

In the preferred embodiment of the present invention, the following expression cassette was constructed to provide the necessary plant regulatory signals (which include the addition of a promoter, 5' untranslated region, translation initiation codon, and polyadenylation signal) to the gene inserts in order to achieve high level expression of the inserts. The expression cassette may be used to express any genes inserted therein. Accordingly, the applicability of the expression cassette goes beyond its use in expressing coat protein genes. Rather, the expression cassette may be used to express any desired protein in transgenic plants. The expression cassette is the preferred expression system for expressing viral coat protein genes in plants.

The expression cassette of the preferred embodiment contains: a constitutive promoter; a 5' untranslated region which enhances gene expression; an initiation codon which comprise Kozak's element; a cloning site where the gene to be expressed may be inserted to produce a functional expression unit; and a 3' untranslated region which comprises a poly(A) addition signal and untranslated flanking regions which result in a higher level of expression.

More specifically, the expression cassette which is the preferred embodiment of the present invention consists of the cauliflower mosaic virus (CaMV) 35S transcript promoter, the 5'-untranslated region of cucumber mosaic virus (CMV), the CMV translation initiation codon, and the CaMV polyadenylation signal. The construction of this expression cassette utilized the Polymerase Chain Reaction (PCR) technique to obtain correct position of the plant regulatory signals and the addition of convenient restriction enzymesites which allow for the easy addition of a coat protein gene and the excision of the completed cassette so it can be transferred to other plasmids.

To accomplish the construction of this expression cassette the following oligomers were synthesized:

1. 5'-GAAGCTTCCGGAAACCTCCTCGGATTCC-3', contains a HindIII site at its 5'-end and contains 21 based which are identical to 21 bases in the 5'-flanking region of CaMV.

2. 5'-GCCATGGTTGACTCGACTCAATTCTACGAC-3', contains a NcoI site at its 5'-end which contains a translation initiation codon which conforms to Kozak's rules and has 21 bases which are identical to 21 bases in the antisense strand of the CMV 5'-untranslated region.

3. 5'-GCCATGGTTGCGCTGAAATCACCAGTCTC-3', contains a NcoI site at its 5'-end (which contains the same translation initiation codon as oligomer 2) and has 20 bases which are identical to 20 bases in the 3'-untranslated region of CaMV.

4. 5'-GAAGCTTGGTACCACTGGATTTTGGTT-3', contains a HindIII site at its 3'-end and has a 20 base match with the flanking DNA region 3' of the CaMV polyadenylation site (on the antisense strand).

Figure 8:
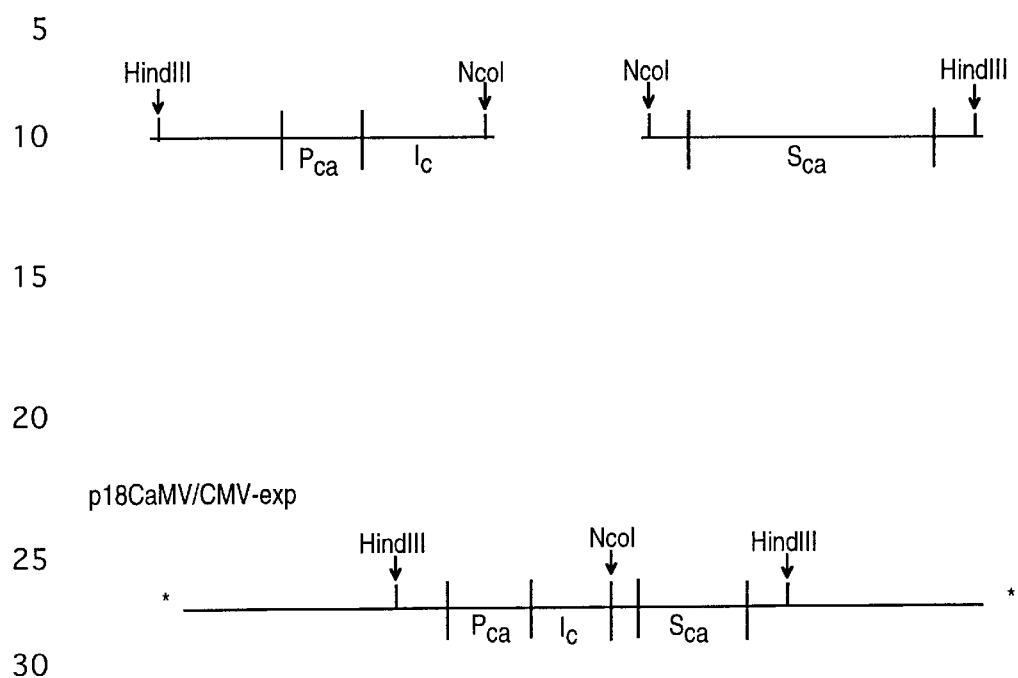
FIG. 8 shows the construction of p18CaMV/CMV-exp.

These oligomers were used to amplify sequences contained within the CMV expression clone referred to as pUC1813/CP19, shown in FIG. 6, and referred to above. As depicted in FIG. 8, the PCR technique was used to amplify the gene regulatory regions in pUC1813/CP19. Amplification of the 5'-flanking, CMV 5'-untranslated region, and CMV initiation codon (which was modified to conform to Kozak's rule AAXXATGG) resulted in a fragment of about 400 base pairs in length and amplification of the CaMV 3-untranslated and flanking regions resulted in a fragment of about 200 base pairs in length. These fragments were digested with NcoI and HindIII, isolated from a polyacrylamide gel, and then ligated into HindIII digested and phosphatase treated pUC18. The resulting clone is referred to as p18CaMV/CMV-exp and is shown in FIG. 8.

EXAMPLE 9

Identification of the WMVII Coat Protein Gene

The cloned WMVII cDNA insert from clone pWMVII-41-3.2 which was produced as decribed above, was sequenced by using both the chemical (Maxam and Gilbert, Methods of Enzymology 65:499, 1980) and enzymatic (Sanger et al., Proc. Natl. Acad. Sci. U.S.A. 74:5463, 1977) methods. Based on this information and comparative analysis with other potyviruses, the nucleotide sequence of clone pWMVII-41-3.2 was found to contain a complete copy of the WMVII coat protein gene. The N-terminus of the coat protein was suggested by the location of the dipeptide sequence Gln-Ser. The length of the WMVII coat protein gene coding region (281 amino acids) is consistent with a gene encoding a protein of about 33 kD. The sequences of this WMVII coat protein gene and protein are shown in FIGS. 2A–2B. In addition, comparison of this sequence with that obtained from the related virus Soybean Mosaic Virus (SMV) strain N described by Eggenberger et al. shows that they share overall about 88% identity and excluding the N-terminal length differences they share about 92.5% identity, see FIG. 5. Because these two virus coat proteins share extensive amino acid identities, expression of the coat protein gene from WMVII is expected to yield plants resistant to WMVII infection and could yield plants resistant to SMV infection.

EXAMPLE 10

Construction of a Plant-expressible WMVII Coat Protein Gene Cassette with CaMV 35S Promoter and Polyadenylation Signal and CMV Intergenic Region and Translation Initiator ATG.

Figure 9:
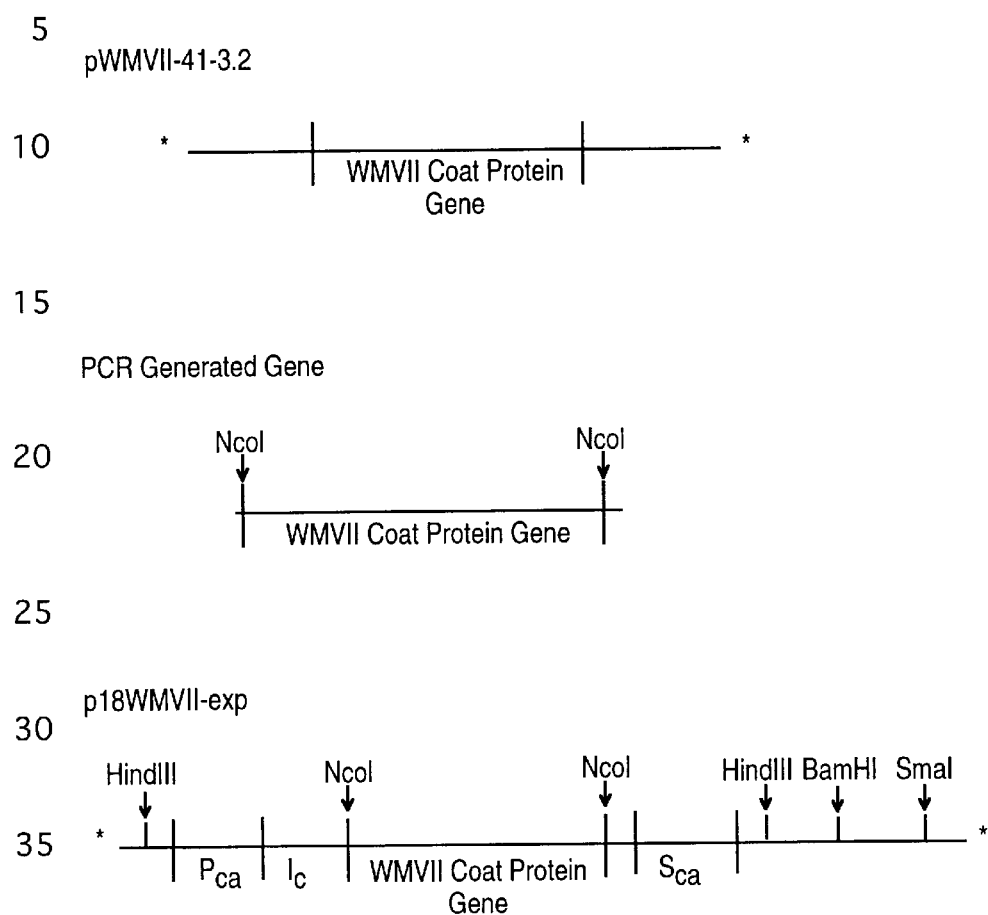
FIG. 9 shows the construction of p18WMVII-exp.

As depicted in FIG. 9, attachment of the necessary plant regulatory signals to the WMVII coat protein gene was accomplished by using the PCR technique to amplify the WMVII coat protein gene using oligomers which would add the necessary sites to its 5' and 3' sequences. Following this amplification the resulting fragment is digested with the appropriate restriction enzyme and cloned in the NcoI site of the above described expression cassette containing plasmid, p18CaMV/CMV-exp. Clones containing the WMVII coat protein gene insert need only be checked to determine correct orientation with respect with the CaMV promoter. However, to ensure that no artifacts have been incorporated during the PCR amplification the entire coat protein gene region is checked by nucleotide sequence analysis.

To obtain the amplified WMVII coat protein gene with NcoI restriction enzyme sites on both ends the following two oligomers were synthesized:

1. 5'-ACCATGGTGTCTTTACAATCAGGAAAAG-3', which adds a NcoI site to the 5'-end of the WMVII coat protein gene and retains the same ATG translation start codon which is present in the expression cassette, p18CaMV/CMV-exp.

2. 5'-ACCATGGCGACCCGAAATGCTAACTGTG-3', which adds a NcoI site to the 3'-end of the WMVII coat protein gene, this site can be ligated into the expression cassette, p18CaMV/CMV-exp.

The cloning of this PCR WMVII coat protein gene, using these two oligomers, into p18CaMV/CMV-exp yields a plant expressible WMVII gene (referred to as p18WMVII-exp) which, following transcription and translation, will generate a WMVII coat protein which is identical to that derived from the WMVII coat protein gene nucleotide sequence, see FIGS. 2A–2B. However, this coat protein will differ, because of necessary genetic engineering to add the ATG initiation codon and by including the last four amino acids of the 54 kD nuclear inclusion protein (which is adjacent to the Glu-Ser protease cleavage site); the amino acids added are Val-Ser-Leu-Glu-N-ter WMVII. The addition of these four amino acid residues should not affect the ability of this coat protein to yield plants which are resistant to WMVII infections, because the N-terminal region of potyvirus and coat proteins appear not to be well conserved for either length or amino acid identity. However, if this is found to be a problem its replacement would involve the use of a different oligomer to obtain N-terminal variations of the WMVII coat protein gene. The cloned construction of the plant expressible WMVII coat protein gene is referred to as p18WMVII-exp, and is shown in FIG. 9.

EXAMPLE 11

Construction of a Micro T-DNA Plasmid Containing the Plant-expressible WMVII Coat Protein Gene Construction.

Figure 10:
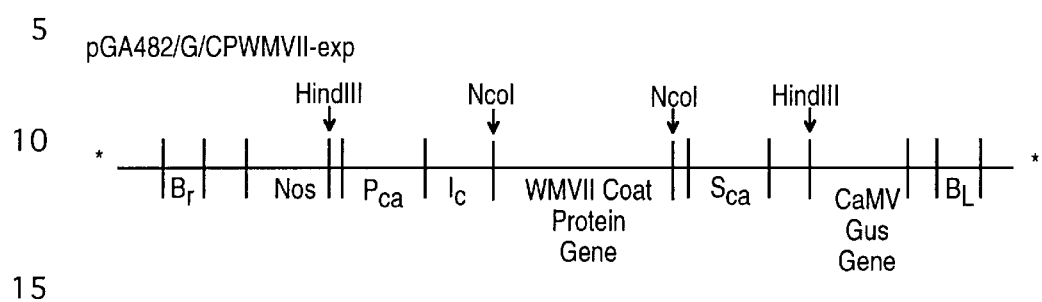
FIG. 10 shows the construction of pGA482/G/CPWMVII-exp.

As depicted in FIG. 10, the plant expression cassette for the WMVII coat protein gene was transferred into a suitable micro-T-DNA vector which contains the necessary Agrobacterium T-DNA transfer signals (to mediated transfer from an Agrobacterium and integration into a plant genome) and wide-host range origin of replication (for replication in Agrobacterium) to form plasmid pGA482/G/CPWMVII-exp. To construct this plasmid, plasmid p18WMVII-exp was digested with Hind III (which cuts within the polycloning sites of pUC18, well outside of the expression cassette), and an 1.8 kb fragment containing the plant-expressible cassette was removed and ligated into the Hind III site of the modified Agrobacterium-derived micro-vector pGA482 (modification included the addition of the β-glucuronidase gene). The micro T-DNA vector, pGA482, is shown in FIG. 7 and available from G. An, Institute of Biological Chemistry, Washington State University, Pullman, Wash. The resulting plasmid was designated, pGA482/G/CPWMVII-exp is shown in FIG. 10. This plasmid (or derivatives thereof) was transferred into virulent or avirulent strains of *Agrobacterium tumefaciens* or rhizogenes, such as A208, C58, LBA4404, C58Z707, A4RS, A4RS(pRiB278b), and others. Strains A208 C58, LBA4404, and A4RS are available from American Type Culture Collection (ATCC), 12301 Parklawn Drive, Rockville, Md. Bacteria A4RS (pRiB278b) is available from Dr. F. Casse-Delbart, C.N.R.A., Routede Saint Cyr. F78000, Versailles, France, Bacteria C58Z707 is available from Dr. A. G. Hepburn, Dept. of Agronomy, University of Illinois, Urbana, Ill.

After transfer of the engineered plasmid pGA482/G/CPWMVII-exp into any of the above listed Agrobacterium strains, these Agrobacterium strains can be used to transfer and integrate within a plant genome of the plant-expressible WMVII coat protein gene contained within its T-DNA region. This transfer can be accomplished using the standard methods for T-DNA transfers which are known to those skilled in the art, or this transfer can be accomplished using the methods described in U.S. patent application Ser. No. 07/135,655 filed Dec. 21, 1987 entitled "Agrobacterium Mediated Transformation of Germinating Plant Seeds". In addition, it has recently been shown that such Agrobacteria are capable of transferring and integrating their T-DNA regions into the genome of soybean plants. Thus these strains could be used to transfer the plant expressible WMVII coat protein gene into the genome of soybean to develop a soybean plant line which is resistant to infection from soybean mosaic virus strains.

EXAMPLE 12

Microprojectile Transfer of pWMVII-exp into Plant Tissues.

Recently an alternative approach for the transfer and integration of DNA into a plant genome has been developed. This technique relies on the use of microprojectiles on which the DNA (plasmid form) is attached. These microprojectiles are accelerated to high velocities and their momentum is used to penetrate plant cell walls and membranes. After penetration into a plant cell the attached DNA leaches off the microprojectile and is transferred to the nucleus where DNA repair enzymes integrate the "free" DNA into the plant genome. In its present form the process is entirely random, but plant tissues which have been successfully transformed by the plasmid DNA (or part of it) can be identified and cultured to homogenity by the use of selectable marker genes (such as the bacterial neomycin phosphotransferase II gene; NPTII), or reporter genes (such as the bacterial beta-glucuronidase gene, Gus). Successful use of particle acceleration to transform plants has recently been shown for soybean and the transfer of p18WMVII-exp into the genome could result in obtaining soybean plants which are resistant to infections from soybean mosaic virus strains.

Figure 11:
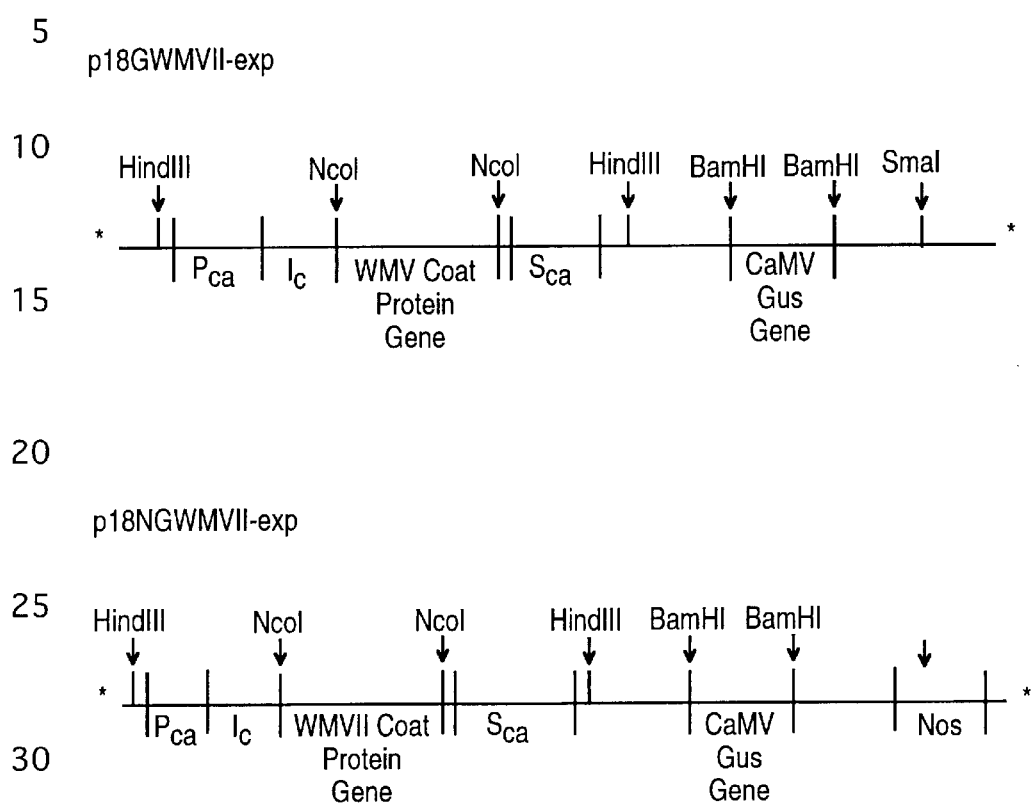
FIG. 11 shows the construction of p18GWMVII-exp and p18NGWMVII-exp.

The use of this process for the transfer of p18WMVII-exp can be accomplished after the addition of either plant expressible genes NPTII or Gus genes or both. Plasmids that have the nptII and Gus genes to p18WMVII-exp are shown in FIG. 11, and referred to as p18GWMVII-exp and p18NTWMVII-exp. In addition, the construction described in Example 11 can also be used for microprojectile transfer as it already has both the nptII and Gus genes attached to the pWMVII-exp cassette (see FIG. 10). The only difficulty which the use of pGA482GG/cpWMVII-exp may encounter during transfer by the microprojectile process is due to its large size, about 18 kb, which may have a lower efficiency transfer and such larger plasmid generally yield less DNA during propagation.

To construct plasmid p18GWMVii-exp. plasmid p18WMVii-exp is digested with BamHI and ligated with a 3.0 kilobase BamHI isolated fragment containing the Gus gene. To construct plasmid p18NGWMVii-exp, the plasmid p18GWMVii-exp is digested with SmaI and ligated with a 2.4 kb isolated fragment containing the Nos-nptII gene generated by digestion with Dra1 and Stu1.

EXAMPLE 13

Identification of the ZYMV Coat Protein Gene.

The cloned ZYMV cDNA insert from clone pZYMV-15, which was cloned using the method described above, was sequenced by using both the chemical (Maxam and Gilbert, Methods of Enzymology 65:499, 1980) and enzymatic (Sanger et al., Proc. Natl. Acad. Sci. U.S.A. 74:5463, 1977) methods. Based on this information and comparative analysis with other potyviruses the nucleotide sequence of clone pZYMV-15 was found to contain a complete copy of the ZYMV coat protein gene. The N-terminus of the coat protein was suggested by the location of the dipeptide sequence Gln-Ser which is characteristic of cleave sites in potyviruses (see Dougherty et al. EMBO J. 7:1281, 1988). The length of the ZYMV coat protein gene coding region (280 amino acids) is consistent with a gene encoding a protein of about 31.3 kD. The sequences of this ZYMV coat protein gene and protein are shown in FIGS. 3A–3B.

EXAMPLE 14

Construction of a Plant-expressible ZYMV Coat Protein Gene Cassette with CaMV 35S Promoter and Polyadenylation Signal and CMV Intergenic Region and Translation Initiator ATG.

Figure 12:
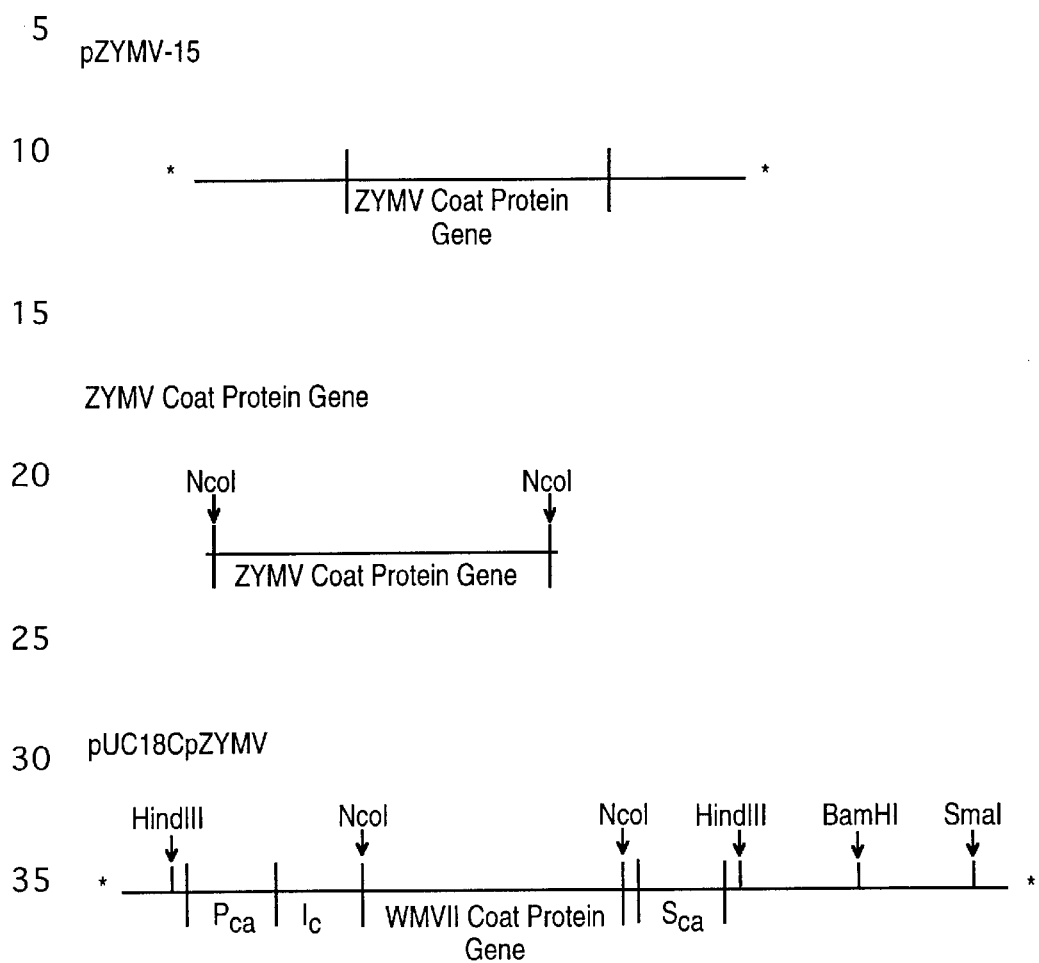
FIG. 12 shows the construction of pUC19CpZYMV.

As depicted in FIG. 12, attachment of the necessary plant regulatory signals to the ZYMV coat protein gene was accomplished by using the PCR technique to amplify the ZYMV coat protein gene using oligomers which would add the necessary sites to its 5' and 3' sequences. Following this amplification the resulting fragment is digested with the appropriate restriction enzyme and cloned into the NcoI site of the above expression cassette containing plasmid, pUC18CP-exp. Clones containing the ZYMV coat protein gene insert need only be checked to determine correct orientation with respect with the CaMV promoter. However, to ensure that no artifacts have been incorporated during the PCR amplification the entire coat protein gene region is checked by nucleotide sequence analysis.

To obtain the amplified ZYMV coat protein gene with NcoI restriction enzyme sites on both ends the following two oligomers were synthesized.

1.

5'-ATCATTCCATGGGCACTCAACCAACTGTGGC-3', which adds a NcoI site to the 5'-end of the ZYMV coat protein gene and retains the same ATG translation start codon which is present in the expression cassette, pUC18cpexp.

2.

5'-AGCTAACCATGGCTAAAGATATCAAATAAAGCTG-3', which adds a NcoI site to the 3'-end of the ZYMV coat protein gene, this site can be ligated into the expression cassette, pUC18cpexp.

The cloning of this PCR ZYMV coat protein gene, using these two oligomers, into pUC18cpexp yields a plant expressible ZYMV gene (referred to as pUC18cpZYMV) which following transcription and translation will generate a ZYMV coat protein which is identical to that derived from the ZYMV coat protein gene nucleotide sequence, see FIG. 3A–3B. However, this coat protein will differ, because of necessary genetic engineering to add the ATG initiation codon followed by Gly, which is the amino acid 3' adjacent to the Ser of the polyprotein cleavage site (see FIG. 3A–3B). The Gly amino acid residue was selected for the potential N-terminal amino acid because many potyvirus coat proteins have either an Ser, Gly, or Ala at their N-terminal. However, if this is found to be a problem its replacement would involve the use of a different oligomer to obtain a different N-terminal amino acid for the ZYMV coat protein. The cloned construction of the plant expressible ZYMV coat protein gene is referred to pUC18cpZYMV, and is shown in FIG. 12.

EXAMPLE 15

Construction of a Micro T-DNA Plasmid Containing the Plant-Expressible ZYMV Coat Protein Gene Construction.

Figure 13:
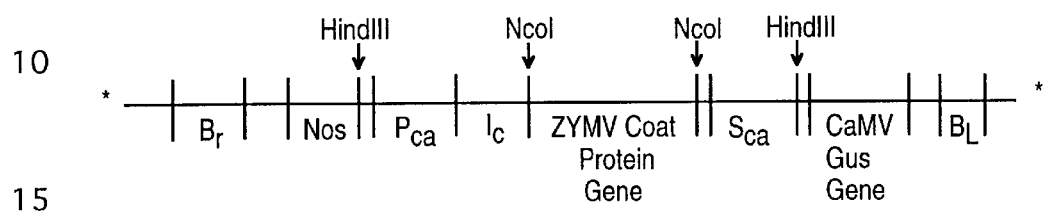
FIG. 13 shows the construction of pGA482/GG/cpZYMV.

Following the teachings of Example 11 with appropriate modifications, the construction of a micro T-DNA plasmid containing a plant-expressible ZYMV coat protein was constructed. Plasmid pUC18cpZYMV (FIG. 12) was digested with HInd III (which cuts within the polycloning sites of pUC18, well outside of the expression cassette), and a 1.6 kb fragment containing the plant-expressible cassette was removed and ligated into the Hind III site of the micro-vector pGA482 (FIG. 7). The resulting plasmid was designated, pGA482GG/cpZYMV is shown in FIG. 13.

After transfer of the engineered plasmid pGA482GG/cpZYMV into Agrobacterium strains, the Agrobacterium strains can be used to transfer and integrate within a plant genome the plant-expressible ZYMV coat protein gene contained within its T-DNA region.

EXAMPLE 16

Microprojectile Transfer of pUC18cpZYMV into Plant Tissues.

Following the teachings of Example 12, the microprojectile transfer technique can be used to introduce the ZYMV coat protein gene with appropriate genetic regulatory sequences into plant tissues.

Figure 14:
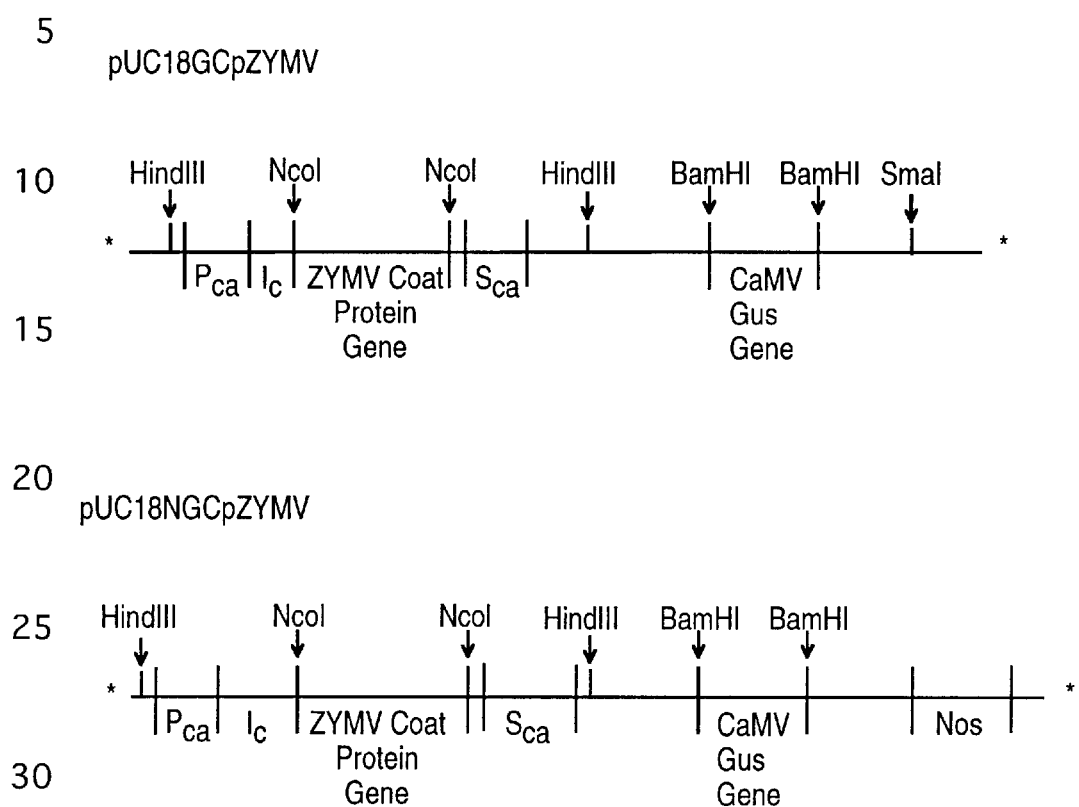
FIG. 14 shows the construction of pUC18GCpZYMV and pUC18NGCpZYMV.

The use of this process for the transfer of pUC18cpZYMV can be accomplished after the addition of either plant expressible genes NPTII or Gus genes or both. Plasmids that have the nptII and Gus genes to pUC18cpZYMV are shown in FIG. 14 and referred to as pUC18GcpZYMV and pUC18NGcpZYMV. In addition, the construction described in Example 15 can also be used for microprojectile transfer as it already has both the nptII and Gus genes attached to the pUC18cpZYMV cassette (see FIG. 13). The only difficulty which the use of pGA482GG/cpZYMV may encounter during transfer by the microprojectile process is due to its large size, about 18 kb, which may have a lower efficiency transfer and such larger plasmid generally yield less DNA during propagation.

To construct plasmid pUC18GCPZYMV, plasmid pUC18CPZYMV is digested with BamHI and ligated to a 3.0 BamHI isolated fragment which contains the Gus gene. To construct plasmid pUC18GCPZYMV, plasmid pUC18GCPZYMV is digested with SmaI and ligated with a 2.4 kb isolated fragment containing the Nos nptII gene isolated by digestion with DraI and StuI.

We claim:

1. A transgenic plant comprising a coat protein gene selected from the group consisting of the Papaya ringspot virus strain papaya ringspot PRV-p coat protein gene having the sequence shown in FIGS. 1A–1B, the Watermelon mosaic virus II WMVII coat protein gene having the sequence shown in FIGS. 2A–2B and the Zucchini yellow mosaic virus ZYMV coat protein gene having the sequence shown in FIGS. 3A–3B and selected from the group consisting of Cucubitaceae, Caricacaeae, Solanaceae and Leguminosae.

2. A transgenic plant according to claim 1 comprising the Papaya ringspot virus strain papaya ringspot PRV-p coat protein gene having the sequence shown in FIGS. 1A–1B.

3. A transgenic plant according to claim 1 comprising the Watermelon mosaic virus II WMVII coat protein gene having the sequence shown in FIGS. 2A–2B.

4. A transgenic plant according to claim 1 comprising the Zucchini yellow mosaic virus ZYMV coat protein gene having the sequence shown in FIGS. 3A–3B.

5. A transgenic plant comprising a DNA molecule of a potyvirus having a DNA sequence selected from the group consisting of:

(1) the sequence contained in FIGS. 1A–1B encoding the coat protein of Papaya ringspot virus strain papaya ringspot PRV-p;

(2) the sequence contained in FIGS. 2A–2B encoding the coat protein of Watermelon mosaic virus II WMVII; and (3) the sequence contained in FIGS. 3A–3B encoding the coat protein of Zucchini yellow mosaic virus ZYMV.

6. A transgenic plant according to claim 5, wherein cells of the plant express DNA of Papaya ringspot virus PRV-p, Watermelon mosaic virus II WMVII, or Zucchini yellow mosaic virus ZYMV.

7. A transgenic plant according to claim 2, 3, or 4, wherein cells of the plant express the viral coat protein DNA.

8. A transgenic plant according to claim 7 wherein said plant possesses greater resistance to infection by a potyvirus than a plant that does not express DNA of Papaya ringspot virus strain papaya ringspot PRV-p, Watermelon mosaic virus II WMVII, or Zucchini yellow mosaic virus ZYMV.

9. A transgenic plant comprising a potyvirus coat protein gene selected from the group consisting of the Papaya ringspot virus strain papaya ringspot PRV-p coat protein gene having the sequence shown in FIGS. 1A–1B, the Watermelon mosaic virus II WMVII coat protein gene having the sequence shown in FIGS. 2A–2B and the Zucchini yellow mosaic virus ZYMV coat protein gene having the sequence shown in FIGS. 3A–3B.

10. Seed from a transgenic plant according to claim 5.

11. Seed from a transgenic plant according to claim 10 wherein the plant is selected from the group consisting of Cucurbitaceae, Caricaceae, Solanaceae, and Leguminosae.

12. Seed from a transgenic plant according to claim 9.

13. Transformed plant cells comprising a DNA molecule of a potyvirus having a DNA sequence selected from the group consisting of:

(1) the sequence contained in FIGS. 1A–1B encoding the coat protein of Papaya ringspot virus strain papaya ringspot PRV-p;

(2) the sequence contained in FIGS. 2A–2B encoding the coat protein of Watermelon mosaic virus II WMVII; and (3) the sequence contained in FIGS. 3A–3B encoding the coat protein of Zucchini yellow mosaic virus ZYMV.

14. Transformed plant cells according to claim 13, wherein the cells express a protein of Papaya ringspot virus PRV-p, Watermelon mosaic virus II WMVII, or Zucchini yellow mosaic virus ZYMV.

* * * * *